(12) United States Patent
Gopalsamy et al.

(10) Patent No.: US 7,563,813 B2
(45) Date of Patent: Jul. 21, 2009

(54) IMINOTHIAZOLIDINONE DERIVATIVES AS SFRP-1 ANTAGONISTS

(75) Inventors: Ariamala Gopalsamy, Mahwah, NJ (US); Mengxiao Shi, New Rochelle, NY (US)

(73) Assignee: Wyeth, Madison, NJ (US)

( * ) Notice: Subject to any disclaimer, the term of this patent is extended or adjusted under 35 U.S.C. 154(b) by 465 days.

(21) Appl. No.: 11/432,229

(22) Filed: May 10, 2006

(65) Prior Publication Data
US 2006/0270720 A1    Nov. 30, 2006

Related U.S. Application Data

(60) Provisional application No. 60/680,690, filed on May 13, 2005.

(51) Int. Cl.
    *A61K 31/427*    (2006.01)
    *C07D 277/04*    (2006.01)
    *C07D 409/12*    (2006.01)

(52) U.S. Cl. .................. 514/370; 548/146; 548/182; 548/184; 514/365; 514/369

(58) Field of Classification Search .......... 548/146, 548/182, 184; 514/365, 369, 370
    See application file for complete search history.

(56) References Cited

U.S. PATENT DOCUMENTS 3,886,150 A    5/1975    Sellstedt et al. .......... 260/243 C

FOREIGN PATENT DOCUMENTS

| WO | 95/17416 A1 | 6/1995 |
|---|---|---|
| WO | 2005/033048 A | 4/2005 |
| WO | 2005/033102 A | 4/2005 |
| WO | 2005/075471 A | 8/2005 |
| WO | 2005/116002 A | 12/2005 |

OTHER PUBLICATIONS

Sellstedt et al (1975): STN International HCAPLUS database, (Columbus, Ohio), Accession No. 1975:547491.*
Hodge et al (2005): STN International HCAPLUS database, (Columbus, Ohio), Accession No. 2005:324155.*
Barth, A. I. M. et al., "Cadherins, catenins and APC protein: interplay between cytoskeletal complexes and signaling pathways," *Curr. Opin. Cell Biol.* 1997, 9, 683-690.
Bodine, P.V.N, et al., "The Wnt Antagonist Secreted Frizzled-Related Protein-1 Is a Negative Regulator of Trabecular Bone Formation in Adult Mice," *Mol. Endocrinol.*, 2004, 18(5) 1222-1237.
Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4), 285-298.
Bundgaard, H., "Means to enhance penetration; Prodrugs as a means to improve the delivery of peptide drugs," *Advanced Drug Delivery Reviews*, 1992, 8, 1-38.

Coghlan, M. P. et al., "Selective small molecule inhibitors of glycogen synthase kinase-3 modulate glycogen metabolism and gene transcription," *Chemistry and Biology*, 2000, 7, 793-803.
Eliel, E. L., *Stereochemistry of Carbon Compounds*, McGraw Hill, NY (1962) Ch. 4, pp. 46-87.
Finch, P. W. et al., "Purification and molecular cloning of a secreted, Frizzled—related antagonist of Wnt action," *Proc. Natl. Acad. Sci. U.S.A.*, 1997, 94, 6770-6775.
Higuchi and Stella (eds.), *Prodrugs as Novel Drug Delivery Systems*, American Chemical Society (1975), pp. 1-115 abd 196-223.
Hoang, B. et al., "Primary Structure and Tissue Distribution of FRZB, a Novel Protein Related to Drosophila Frizzled, Suggest a Role in Skeletal Morphogenesis," *J. Biol. Chem.* 1996, 271, 26131-26137.
Jacques, J. et al., *Enantiomers, Racemates and Resolutions*, Wiley Interscience, NY (1981) pp. 251-434.
Krogsgaard-Larsen, et al., (ed). *Design and Application of Prodrugs, Textbook of Drug Design and Development*, Chapter 5, 113-191 (1991).
Moon, R. T. et al., "Structurally Related Receptors and Antagonists Complete for Secreted Wnt Ligands," *Cell* 1997, 88, 725-728.
Nusse, R. and Varmus, E., "Wnt Genes," *Cell*, 1992, 69, 1073-1087.
*Remington's Pharmaceutical Sciences*, 17th Ed., Gennaro, A. R. (Ed.), Mack Publishing Company, Easton, PA (1985) pp. 1409-1677.
Widder, et al. (ed.), *Methods in Enzymology*, vol. 112, Academic Press (1985), pp. 309-323.
Wilen, S.H. *Tables of Resolving Agents and Optical Resolutions*, pp. 268-298, E.L. Eliel, Ed., University of Notre Dame Press, Notre Dame, IN 1972.
Wilen, S.H., et al., "Strategies in optical resolutions," *Tetrahedron*, 33, 2725-2736, 1977.

(Continued)

*Primary Examiner*—Golam M Shameem
(74) *Attorney, Agent, or Firm*—Joel Silver; Paul Carango

(57) ABSTRACT

Compounds of Formula 1, or pharmaceutically acceptable salts thereof, are provided:

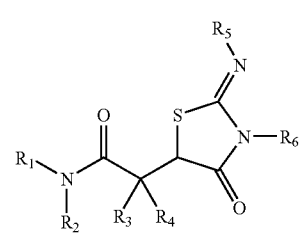

(1)

which are inhibitors of secreted frizzled related protein-1. The compounds, and compositions containing the compounds, can be used to treat a variety of disorders, including osteoporosis.

24 Claims, No Drawings

OTHER PUBLICATIONS

Database Chemcats Chemical Abstracts Service, Columbus, Ohio, US; XP002398682 retrieved from STN; Accession No. 2005: 1630334, 2005: 1149773, 2005: 1514390, 2005: 1514389, 2005: 1514388, 2005: 1135780, 2005: 1614233, 2005: 1133896, 2005: 1481781, 2005: 1115929, 2005: 1115925, 2005: 1115689, 2005: 1600586, 2005: 160066, 2005: 1600065, 2005: 1600064, 2005: 1600062, 2005: 1097802, 2005: 1426136, 2005: 1000330, 2005: 997120, 2005: 989623, and 2005: 989622 & *Interchim Intermediates* (Catalog) Jan. 18, 2005, Order No. F1312-0044, BAS 08951505, AP-906/42287275, AP-906/42287274, AP-906/42287143, BAS 06262542, F1637-0006, BAS 07438802, AP-906/41651019, BAS 04357868, BAS 04357893, BAS 02915843, F1248-0027, F1199-0126, F1199-0133, F1199-0114, F119-0134, BAS 03570784, AF-339/37271008, BAS 03571151, BAS 03571436, BAS 03571475, and BAS 03571474.

Augustin, M. et al., "Synthese von N-Maleoyl-aminosäuren und -peptiden," *Journal Fuer Praktische Chemie*, 1985, 327(5), 789-798, XP000563404.

Augustin, M. et al., "Umsetzung von N-substitutierten Maleinimiden mit Thioharnstoffen und polarographische Untersuchung des Reaktionsablaufs," *Zeitschrift Fuer Chemie*, 1974, 14(7), 434-435, XP008068848.

Arakelian, A. N. et al., "2-Imino-4-oxo-5-thiazolidineacetic acid and its derivatives," *Journal of Organic Chemistry*, Mar. 1960, 25(3), 465-467, XP002398678.

Bethell, J. R. et al., "Organic reactions in aqueous solution at room temperature. Part II. The influence of pH on Condensations involving the linking of carbon to carbon, of carbon to nitrogen, and of carbon to sulphur," *Journal of the Chemical Society*, 1961, 5211-5216, XP002398679.

Balasubramaniyan, V. et al., "Heterocyclisation of maleic anhydride derivatives with thiourea: synthesis of 5-substituted-2-imino-4-oxo-thiazolidines," *Indian Journal of Chemistry Section B*, Dec. 1990, 29b, 1092-1096, XP008068847.

\* cited by examiner

IMINOTHIAZOLIDINONE DERIVATIVES AS SFRP-1 ANTAGONISTS

CROSS REFERENCE TO RELATED APPLICATIONS

This application claims the benefit of U.S. application Ser. No. 60/680,690, filed May 13, 2005, which is incorporated herein in its entirety.

FIELD OF THE INVENTION

The present invention relates to novel iminothiazolidinone derivatives that act, for example, as inhibitors of secreted frizzled-related protein-1. The present invention also relates to processes for the preparation of iminothiazolidinone derivatives and to their use in treating various diseases and disorders.

BACKGROUND OF THE INVENTION

Bone remodeling, the process by which the adult human skeleton is continuously renewed, is carried out by osteoclasts and osteoblasts, two specialized cell types that originate from hematopoietic and mesenchymal progenitors of the bone marrow, respectively. A continuous and orderly supply of these cells is believed to be essential for skeletal homeostasis, as increased or decreased production of osteoclasts or osteoblasts and/or changes in the rate of their apoptosis are largely responsible for the imbalance between bone resorption and formation that underlies several systemic or localized bone diseases. For example, enhanced osteoclast activity has been found to play a major role in the pathogenesis of postmenopausal osteoporosis, Paget's disease, lytic bone metastases, multiple myeloma, hyperparathyroidisn, rheumatoid arthritis, periodontitis, and hypercalcemia of malignancy.

Numerous genes and gene families (and the polypeptides encoded by them) that participate in the regulation of bone cell production and apoptosis have been identified. Wnt proteins have been identified as a family of growth factors consisting of more than a dozen structurally related molecules that are involved in the regulation of fundamental biological processes such as apoptosis, embryogenesis, organogenesis, morphogenesis and tumorigenesis (Nusse and Varmus, *Cell* 1992, 69:1073-1087). Wnt polypeptides are multipotent factors and have biological activities similar to those of other secretory proteins such as transforming growth factor (TGF)-β, fibroblast growth factors (FGFs), nerve growth factor (NGF), and bone morphogenetic proteins (BMPs). One member of the Wnt growth factor family, termed Wnt-x, is preferentially expressed in bone tissue and in bone-derived cells and appears to be involved in maintaining the mature osteoblast (bone-forming cell) phenotype (WO 95/17416).

Studies indicate that certain Wnt proteins interact with a family of proteins named "frizzled" that act as receptors for Wnt proteins or as components of a Wnt receptor complex (in Moon et al., *Cell* 1997, 88:725-728; Barth et al., *Curr. Opin. Cell Biol.* 1997, 9:683-690). Frizzled proteins contain an amino terminal signal sequence for secretion, a cysteine-rich domain (CRD) that is thought to bind Wnt, seven putative transmembrane domains that resemble a G-protein coupled receptor, and a cytoplasmic carboxyl terminus.

The first secreted frizzled-related protein (SFRP) was named "Frzb" (for "frizzled motif in bone development") and was purified and cloned from bovine articular cartilage extracts based on its ability to stimulate in vivo chondrogenic activity in rats (Hoang et al., *J. Biol. Chem.* 1996, 271:26131-26137). The human homologue of the bovine gene has also been cloned. Unlike the frizzled proteins, however, Frzb does not contain a serpentine transmembrane domain, and appears to be a secreted receptor for Wnt. The Frzb cDNA encodes a 325 amino acid/36,000 dalton protein and is predominantly expressed in the appendicular skeleton. The highest level of expression is in developing long bones and corresponds to epiphyseal chondroblasts; expression declines and disappears toward the ossification center.

Studies indicate that SFRPs participate in apoptosis. Some SFRPs have thus been identified as "SARPs" for secreted apoptosis related proteins. Additional members of the SFRP family have been identified, and have been shown to be antagonists of Wnt action. There are currently at least five known human SFRP/SARP genes: SFRP-1/FrzA/FRP-1/SARP-2, SFRP-2/SDF-5/SARP-1, SFRP-3/Frzb-1/FrzB/Fritz, SFRP-4 and SFRP-5/SARP-3 (Leimeister et al., *Mechanisms of Development* 1998, 75:29-42). Secreted frizzled related protein-1 (SFRP-1) is a Wnt antagonist and is expressed in osteoblasts and osteocytes. Although the precise role that SARPs/SFRPs play in apoptosis is not yet clear, these proteins appear to either suppress or enhance the programmed cell death process. Deletion of SFRP-1 in mice has been shown to lead to decreased osteoblast/osteocyte apoptosis and to increased bone formation. (Bodine, P. V. N, et al., *Mol. Endocrinol.*, 2004, 18(5) 1222-1237.)

A need exists in the art for the identification of inhibitors of SFRP-1 that can be used as novel agents for the treatment of bone disorders, including bone resorption disorders such as osteoporosis, and for regulation of bone formation in humans.

SUMMARY OF THE INVENTION

The present invention relates to certain iminothiazolidinone derivatives and to their use, for example, in medical treatment. In one aspect, the invention relates to iminothiazolidinone derivatives that act as antagonists of secreted frizzled related protein-1. The compounds can be used, for example, to treat bone disorders such as osteoporosis.

In certain aspects, the present invention is directed to compounds of Formula 1:

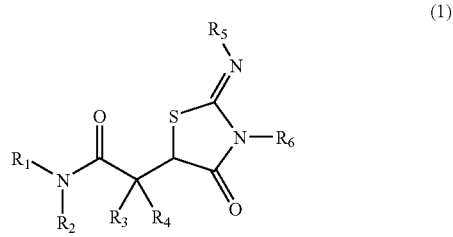

(1)

and pharmaceutically acceptable salts thereof, wherein $R_1$ and $R_2$ are, independently, hydrogen; straight chain alkyl of 1 to 8 carbon atoms; branched chain alkyl of 3 to 12 carbons atoms; alkenyl of 2 to 8 carbon atoms; cycloalkyl or bicycloalkyl of 3 to 12 carbon atoms; heterocycloalkyl or heterobicycloalkyl of 3 to 12 ring atoms having 1 to 3 heteroatoms independently selected from nitrogen, oxygen, and sulfur; aryl of 6 to 10 carbon atoms; or heteroaryl of 5 to 10 ring atoms having 1 to 3 heteroatoms independently selected from nitrogen, oxygen, and sulfur; and $R_3$, $R_4$, $R_5$, and $R_6$ are, independently, hydrogen; straight chain alkyl of 1 to 8 carbon atoms; branched chain alkyl of 3 to 12 carbons atoms; straight chain alkenyl of 2 to 8 carbon atoms; branched chain alkenyl of 3 to 12 carbons atoms; straight chain alkynyl of 2 to 8 carbon atoms; branched chain alkynyl of 5 to 12 carbons atoms; or cycloalkyl of 3 to 12 carbon atoms.

In other embodiments, the invention relates to compositions comprising at least one compound of Formula 1, or a pharmaceutically acceptable salt thereof, and one or more pharmaceutically acceptable excipients, diluents, or carriers.

The present invention also provides methods for treating patients suffering from osteoporosis, arthritis, chronic obstructive pulmonary disease, cartilage defect repair, or leiomyoma that comprise administering to the patients a therapeutically effective amount of at least one compound of Formula 1.

DETAILED DESCRIPTION OF ILLUSTRATIVE EMBODIMENTS

The term "alkyl," as used herein, refers to an aliphatic hydrocarbon chain having 1 to 12 carbon atoms, preferably 1 to 8 carbon atoms, more preferably 1 to 3 carbon atoms. The term "alkyl" includes, but is not limited to, straight and branched chains such as methyl, ethyl, n-propyl, isopropyl, n-butyl, isobutyl, sec-butyl, t-butyl, n-pentyl, isopentyl, neopentyl, n-hexyl, and isohexyl. In some embodiments, the alkyl group is preferably branched having 3 to 12 carbon atoms.

The term "perfluoroalkyl," as used herein, refers to a straight or branched aliphatic hydrocarbon chain of 1 to 8 carbon atoms, preferably 1 to 3 carbon atoms, in which all hydrogens are replaced with fluorine.

The term "alkenyl," as used herein, refers to a straight or branched hydrocarbon chain having 2 to 12 carbon atoms and 1 to 3 double bonds. Examples of alkenyl groups include vinyl, prop-1-enyl, allyl, methallyl, but-1-enyl, but-2-enyl, but-3-enyl, or 3,3-dimethylbut-1-enyl. In some embodiments, the alkenyl group is a straight chain alkenyl group of 2 to 8 carbon atoms or a branched chain alkenyl group of 3 to 12 carbon atoms.

The term "alkynyl," as used herein, refers to a straight or branched hydrocarbon chain having 2 to 12 carbon atoms that contains 1 to 3 triple bonds. In some embodiments, the alkynyl group is preferably a straight chain alkynyl group of 2 to 8 carbon atoms or a branched chain alkynyl group of 5 to 12 carbon atoms.

The term "cycloalkyl," as used herein, refers to a hydrocarbon ring containing 3 to 12 carbon atoms, preferably 3 to 5 carbon atoms. Cycloalkyl groups may be saturated or partially saturated and may be monocyclic or bicyclic. Bicyclic cycloalkyl groups can be bridged. "Bridged" cycloalkyl groups contain at least one carbon-carbon bond between two non-adjacent carbon atoms of the cycloalkyl ring. The cycloalkyl group may be unsubstituted or substituted.

The term "heterocycloalkyl," as used herein, refers to a 3 to 12 membered, and more preferably a 5 to 7 membered, cycloalkyl group in which one to three carbon atoms of the cycloalkyl group are replaced with one to three heteroatoms independently selected from oxygen, nitrogen, and sulfur. The heterocycloalkyl group may be saturated or partially saturated, and may be monocyclic or bicyclic (such as bridged). Preferably, the heterocycloalkyl group is monocyclic. The heterocycloalkyl group may be unsubstituted or substituted.

The term "aryl," as used herein refers to a 6 to 10 membered carbocyclic aromatic ring. Aryl groups may be monocyclic or bicyclic, and may be substituted or unsubstituted. Monocyclic aryl groups preferably have 6 or 7 members and bicyclic aryl groups preferably have 8, 9 or 10 members. Exemplary aryl groups include phenyl and naphthyl.

The term "heteroaryl" as used herein, refers to a 5 to 10 membered monocyclic or bicyclic carbon containing aromatic ring having 1 to 3 of its ring atoms independently selected from nitrogen, sulfur and oxygen. Monocyclic rings preferably have 5 to 6 members and bicyclic rings preferably have 8 to 10 members. The heteroaryl group may be unsubstituted or substituted. Examples of heteroaryl groups include, but are not limited to, thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, and nazolinyl groups. Where the heteroaryl group is bicyclic, the group may comprise a monocyclic heteroaryl group fused to a non-aromatic ring.

The term "acyl," as used herein, refers to the group —C(O)R' where R' is an alkyl group of 1 to 6 carbon atoms as previously defined.

The terms "halogen" or "halo," as used herein, refer to chlorine, bromine, fluorine or iodine.

The terms "alkylamino" and "N,N-dialkylamino," as used herein, respectively, refer to —NHR' and —N(R')$_2$, where R' is an alkyl group of 1 to 8 carbon atoms, preferably 1 to 3 carbon atoms, as previously defined.

The term "aminoalkyl," as used herein, refers to the group —R'NH$_2$ where R' is an alkyl group as previously defined.

The term "cycloalkylamino," as used herein, refers to the group —NH-cycloalkyl where "cycloalkyl" is a cycloalkyl group as previously defined.

The term "arylamino," as used herein, refers to the group —NH-aryl where "aryl" is an aryl group as previously defined.

The term "haloarylamino," as used herein, refers to the group —NH-aryl-halo where "halo" is a halogen atom as previously defined and "aryl" is an aryl group as previously defined.

The term "alkylthio," as used herein, refers to the group —S—R' where R' is an alkyl group as previously defined.

The term "arylthio," as used herein, refers to the group —S-aryl where "aryl" is an aryl group as previously defined.

The term "alkoxy," as used herein, refers to the group —O—R' where R' is an alkyl group of 1 to 8 carbon atoms, preferably 1 to 3 carbon atoms, as previously defined.

The term "perfluoroalkoxy," as used herein, refers to the group —O—R" where R" is a perfluoroalkyl group of 1 to 8 carbon atoms, preferably 1 to 3 carbon atoms, as previously defined.

The term "aryloxy," as used herein, refers to the group —O-aryl where "aryl" is an aryl group as previously defined.

The term "fused cycloalkylthiopheneyl," as used herein, refers to a thiophene group to which a saturated or partially saturated cycloalkyl group, as previously defined, is fused to form a bicyclic structure.

The term "partially saturated," as used herein, refers to a nonaromatic cycloalkyl or heterocycloalkyl group containing at least one double bond and preferably one or two double bonds.

The term "therapeutically effective amount," as used herein, refers to an amount of a compound that, when administered to a patient, is effective to at least partially treat a condition from which the patient is suffering or is suspected to suffer. Such conditions include, but are not limited to, osteoporosis, arthritis, chronic obstructive pulmonary disease, cartilage defect repair, and leiomyoma.

The term "pharmaceutically acceptable salts" or "pharmaceutically acceptable salt" refers to salts derived by treating a compound of Formula 1 with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

The term "patient," as used herein, refers to a mammal.

The terms "administer," "administering," or "administration," as used herein, refer to either: (i) administering a compound or composition to a patient, or (ii) administering a to a patient another compound which will form the compound of interest within the patient's body.

The terms "treat" and "treating," as used herein, refer to partially or completely alleviating, inhibiting, preventing, ameliorating and/or relieving a condition from which a patient is suspected to suffer.

The terms "suffer" and "suffering," as used herein, refer to one or more conditions with which a patient has been diagnosed, or is suspected to have.

Certain embodiments of the invention relate to compounds of Formula 1:

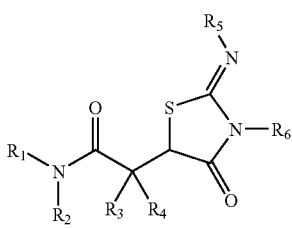

(1)

and pharmaceutically acceptable salts thereof, wherein $R_1$ and $R_2$ are, independently, hydrogen; straight chain alkyl of 1 to 8 carbon atoms; branched chain alkyl of 3 to 12 carbons atoms; alkenyl of 2 to 8 carbon atoms; cycloalkyl or bicycloalkyl of 3 to 12 carbon atoms; heterocycloalkyl or heterobicycloalkyl of 3 to 12 ring atoms having 1 to 3 heteroatoms independently selected from nitrogen, oxygen, and sulfur; aryl of 6 to 10 carbon atoms; or heteroaryl of 5 to 10 ring atoms having 1 to 3 heteroatoms independently selected from nitrogen, oxygen, and sulfur; and $R_3$, $R_4$, $R_5$, and $R_6$ are, independently, hydrogen; straight chain alkyl of 1 to 8 carbon atoms; branched chain alkyl of 3 to 12 carbons atoms; straight chain alkenyl of 2 to 8 carbon atoms; branched chain alkenyl of 3 to 12 carbons atoms; straight chain alkynyl of 2 to 8 carbon atoms; branched chain alkyl of 5 to 12 carbons atoms; or cycloalkyl of 3 to 12 carbon atoms.

With respect to $R_1$ and $R_2$, the straight chain alkyl, cycloalkyl, bicycloalkyl, heterocycloalkyl, heterobicycloalkyl, aryl and heteroaryl groups are optionally substituted with 1 to 5 substituents independently selected from: straight chain alkyl of 1 to 8 carbon atoms; branched chain alkyl of 3 to 12 carbon atoms; alkenyl of 2 to 8 carbon atoms; alkynyl of 2 to 8 carbon atoms; cycloalkyl of 3 to 12 carbon atoms; heterocycloalkyl of 3 to 12 ring atoms having 1 to 3 heteroatoms independently selected from nitrogen, oxygen, and sulfur; aryl of 6 to 10 carbon atoms; heteroaryl of 5 to 10 ring atoms having 1 to 3 heteroatoms independently selected from nitrogen, oxygen, and sulfur; alkoxy of 1 to 8 carbon atoms, perfluoroalkoxy of 1 to 8 carbon atoms; phenyloxy; alkylthio of 1 to 8 carbon atoms; acyl of 2 to 7 carbon atoms; phenylcarbonyl; —C(O)OR; —CONR$_2$; —N(R)COR; halogen; cyano (each R being independently selected from hydrogen, a straight chain alkyl of 1 to 8 carbon atoms; and a branched chain alkyl of 3 to 12 carbons atoms); and nitro.

The straight chain alkyl, cycloalkyl, bicycloalkyl, heterocycloalkyl, and heterobicycloalkyl substituents on the straight chain alkyl, cycloalkyl, bicycloalkyl, heterocycloalkyl, heterobicycloalkyl, aryl, and heteroaryl groups of $R_1$ and $R_2$ are themselves optionally substituted with 1 to 5 substituents independently selected from aryl of 6 to 10 carbon atoms; arylamino of 6 to 10 carbon atoms; haloarylamino of 6 to 10 carbon atoms; alkylamino of 1 to 8 carbon atoms; cycloalkylamino of 3 to 12 carbon atoms; arlyoxy of 6 to 10 carbon atoms; alkoxy of 1 to 8 carbon atoms; arylthio of 6 to 10 carbon atoms; alkylthio of 1 to 8 carbon atoms; Br; Cl; and Fl.

Also, the aryl and heteroaryl substituents on the straight chain alkyl, cycloalkyl, bicycloalkyl, heterocycloalkyl, heterobicycloalkyl, aryl, and heteroaryl groups of $R_1$ and $R_2$ are themselves optionally substituted with 1 to 5 substituents independently selected from alkyl of 1 to 8 carbon atoms; perfuloroalkyl of 1 to 8 carbon atoms; Fl; Cl; and Br.

With respect to $R_3$, $R_4$, $R_5$, and $R_6$, the straight chain alkyl groups are optionally substituted with 1 to 5 substituents independently selected from aryl of 6 to 10 carbon atoms; heteroaryl of 5 to 10 ring atoms having 1 to 3 heteroatoms independently selected from oxygen, nitrogen, and sulfur; cycloalkyl of 3 to 12 carbon atoms; and heterocycloalkyl of 3 to 12 ring atoms having 1 to 3 heteroatoms independently selected from oxygen, nitrogen, and sulfur.

In addition, the aryl, heteroaryl, cycloalkyl, and heterocycloalkyl substituents on the straight chain alkyl groups of $R_3$, $R_4$, $R_5$, and $R_6$ are themselves optionally substituted with one to five substituents independently selected from halogen; straight chain alkyl of 1 to 6 carbon atoms; branched chain alkyl of 3 to 6 carbon atoms; perfluoroalkyl of 1 to 3 carbon atoms; perfluoroalkoxy of 1 to 3 carbon atoms; alkoxy of 1 to 6 carbon atoms; aminoalkyl of 1 to 8 carbon atoms; N,N-dialklyamino of 1 to 8 carbon atoms; —C(O)OR; —CONR$_2$; and —N(R)COR.

In preferred embodiments of the invention, $R_1$ of Formula 1 is a phenyl, thiopheneyl, methyl, or fused cycloalkylthiopheneyl group. In particularly preferred embodiments, $R_1$ is a phenyl or thiopheneyl group.

Certain aspects of the invention relate to compounds of Formula 1 in which $R_2$ is hydrogen.

Other aspects of the invention are directed to compounds of Formula 1 in which $R_3$ and $R_4$ are each hydrogen.

Additional embodiments of the invention relate to compounds of Formula 1 in which $R_5$ and $R_6$ are, independently, hydrogen or straight chain alkyl of 1 to 3 carbon atoms. In preferred embodiments of the invention, $R_5$ and $R_6$ are each hydrogen.

Particularly preferred compounds of Formula 1 are those in which $R_1$ is a phenyl or thiopheneyl group, $R_2$, $R_3$, and $R_4$ are each hydrogen, and $R_5$ and $R_6$ are, independently, hydrogen or straight chain alkyl of 1 to 3 carbon atoms.

In certain embodiments of the invention, $R_1$ is a group of the following Formula 2:

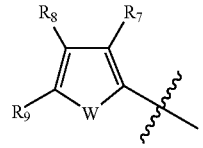

(2)

wherein $R_7$ is hydrogen; straight chain alkyl of 1 to 8 carbon atoms; branched chain alkyl of 3 to 12 carbons atoms; alkenyl of 2 to 8 carbon atoms; cycloalkyl of 3 to 12 carbon atoms; heterocycloalkyl of 3 to 12 ring atoms having 1 to 3 heteroatoms independently selected from nitrogen, oxygen, and sulfur; aryl of 6 to 10 carbon atoms; heteroaryl of 5 to 10 ring atoms having 1 to 3 heteroatoms independently selected from nitrogen, oxygen, and sulfur; —C(O)OR; —CONR$_2$; —N(R)COR; or halogen;

$R_8$ and $R_9$ are, independently, hydrogen; straight chain alkyl of 1 to 8 carbon atoms; branched chain alkyl of 3 to 12 carbons atoms; alkenyl of 2 to 8 carbon atoms; cycloalkyl of 3 to 12 carbon atoms; heterocycloalkyl of 3 to 12 ring atoms having 1 to 3 heteroatoms independently selected from oxygen, nitrogen, and sulfur; aryl of 6 to 10 carbon atoms; heteroaryl of 5 to 10 ring atoms having 1 to 3 heteroatoms independently selected from nitrogen, oxygen, and sulfur; —C(O)OR; —CONR$_2$; —N(R)COR; or halogen;

or $R_8$ and $R_9$, together with the carbon atoms to which they are attached, form a cycloalkyl, heterocycloalkyl, aryl, or heteroaryl group of 5 to 9 atoms, wherein the heterocycloalkyl and heteroaryl groups have 1 to 3 heteroatoms independently selected from oxygen, nitrogen, and sulfur;

W is S, O, or N—$R_{10}$; and $R_{10}$ is hydrogen, straight chain alkyl of 1 to 8 carbon atoms; branched chain alkyl of 3 to 12 carbons atoms; alkenyl of 2 to 8 carbon atoms; cycloalkyl of 3 to 12 carbon atoms; aryl of 6 to 10 carbon atoms; or heteroaryl of 5 to 10 ring atoms having 1 to 3 heteroatoms independently selected from nitrogen, oxygen, and sulfur.

With respect to $R_7$, the straight chain alkyl, cycloalkyl, heterocycloalkyl, aryl, and heteroaryl groups are optionally substituted with 1 to 5 substituents independently selected from straight chain alkyl of 1 to 8 carbon atoms; aryl of 6 to 10 carbon atoms; halogen; alkoxy of 1 to 6 carbon atoms; perfluoroalkyl of 1 to 3 carbon atoms; perfluoroalkoxy of 1 to 3 carbon atoms; aminoalkyl of 1 to 8 carbon atoms; N,N-dialkylamino of 1 to 8 carbon atoms; —C(O)OR; —CONR$_2$; and —N(R)COR. In addition, the straight chain alkyl substituents on the straight chain alkyl, cycloalkyl, heterocycloalkyl, aryl, and heteroaryl groups of $R_7$ are themselves optionally substituted with 1 to 5 substituents independently selected from alkoxy of 1 to 6 carbon atoms; aminoalkyl of 1 to 8 carbon atoms; N,N-dialkylamino of 1 to 8 carbon atoms; —C(O)OR; —CONR$_2$; and —N(R)COR.

With respect to $R_8$ and $R_9$, the straight chain alkyl groups are optionally substituted with 1 to 5 substituents independently selected from aryl of 6 to 10 carbon atoms; arylamino of 6 to 10 carbon atoms; alkylamino of 1 to 8 carbon atoms; arlyoxy of 6 to 10 carbon atoms; alkoxy of 1 to 8 carbon atoms; arylthio of 6 to 10 carbon atoms; and alkylthio of 1 to 8 carbon atoms. In addition, the cycloalkyl, heterocycloalkyl, aryl and heteroaryl groups of $R_8$ and $R_9$ are optionally substituted with 1 to 5 substituents independently selected from straight chain alkyl of 1 to 8 carbon atoms; halogen; alkoxy of 1 to 6 carbon atoms; perfluoroalkyl of 1 to 3 carbon atoms; perfluoroalkoxy of 1 to 3 carbon atoms; aminoalkyl of 1 to 8 carbon atoms; N,N-dialkylamino of 1 to 8 carbon atoms; —C(O)OR; —CONR$_2$; and —N(R)COR. Also, the straight chain alkyl substituents on the straight chain alkyl, cycloalkyl, heterocycloalkyl, aryl, and heteroaryl groups of $R_8$ and $R_9$ are themselves optionally substituted with 1 to 5 substituents independently selected from alkoxy of 1 to 6 carbon atoms; aminoalkyl of 1 to 8 carbon atoms; N,N-dialkylamino of 1 to 8 carbon atoms; —C(O)OR; —CONR$_2$; and —N(R)COR.

In addition, the cycloalkyl, heterocycloalkyl, aryl, and heteroaryl groups formed from $R_8$ and $R_9$, together with the carbon atoms to which they are attached, are optionally substituted with 1 to 5 substituents independently selected from straight chain alkyl of 1 to 8 carbon atoms; halogen; alkoxy of 1 to 6 carbon atoms; perfluoroalkyl of 1 to 3 carbon atoms; perfluoroalkoxy of 1 to 3 carbon atoms; aminoalkyl of 1 to 8 carbon atoms; N,N-dialkylamino of 1 to 8 carbon atoms; —C(O)OR; —CONR$_2$; and —N(R)COR. Moreover, the straight chain alkyl substituents on the cycloalkyl, heterocycloalkyl, aryl, and heteroaryl groups formed from $R_8$ and $R_9$ together with the carbon atoms to which they are attached, are themselves optionally substituted with 1 to 5 substituents independently selected from alkoxy of 1 to 6 carbon atoms; aminoalkyl of 1 to 8 carbon atoms; N,N-dialkylamino of 1 to 8 carbon atoms; —C(O)OR; —CONR$_2$; and —N(R)COR.

With respect to $R_{10}$, the straight chain alkyl groups are optionally substituted with 1 to 5 substituents independently selected from aryl of 6 to 10 carbon atoms; alkoxy of 1 to 6 carbon atoms; aminoalkyl of 1 to 8 carbon atoms; N,N-dialkylamino of 1 to 8 carbon atoms; —C(O)OR; —CONR$_2$; and —N(R)COR. In addition, the aryl and heteroaryl groups of $R_{10}$ are optionally substituted with 1 to 5 substituents independently selected from straight chain alkyl of 1 to 8 carbon atoms; halogen; alkoxy of 1 to 6 carbon atoms; perfluoroalkyl of 1 to 3 carbon atoms; perfluoroalkoxy of 1 to 3 carbon atoms; aminoalkyl of 1 to 8 carbon atoms; N,N-dialkylamino of 1 to 8 carbon atoms; —C(O)OR; —CONR$_2$; and —N(R)COR. Moreover, the straight chain alkyl substituents on the aryl and heteroaryl groups of $R_{10}$ are themselves optionally substituted with 1 to 5 substituents independently selected from alkoxy of 1 to 6 carbon atoms; aminoalkyl of 1 to 8 carbon atoms; N,N-dialkylamino of 1 to 8 carbon atoms; —C(O)OR; —CONR$_2$; and —N(R)COR.

Preferred compounds of Formula 1 are those in which $R_1$ is a group of Formula 2 and $R_2$ is hydrogen. Other preferred compounds are those in which $R_1$ is a group of Formula 2 and $R_3$ and $R_4$ are each hydrogen. Still further preferred compounds of Formula 1 are those in which $R_1$ is a group of Formula 2 and $R_5$ and $R_6$ are, independently, hydrogen or a straight chain alkyl of 1 to 3 carbon atoms.

In particularly preferred compounds, $R_1$ of Formula 1 is a group of Formula 2, $R_2$, $R_3$, and $R_4$ are each hydrogen, and $R_5$ and $R_6$ are, independently, hydrogen or a straight chain alkyl of 1 to 3 carbon atoms.

Specific, representative compounds of Formula 1 include:

ethyl 2-{[(2-amino-4-oxo-4,5-dihydro-1,3-thiazol-5-yl) acetyl]amino}-4,5-dimethylthiophene-3-carboxylate;

N-(3-bromophenyl)-2-(2-imino-4-oxo-1,3-thiazolidin-5-yl) acetamide;

N-(3-fluorophenyl)-2-(2-imino-4-oxo-1,3-thiazolidin-5-yl) acetamide;

N-(3-cyanophenyl)-2-(2-imino-4-oxo-1,3-thiazolidin-5-yl)acetamide;
N-[3-(acetylamino)phenyl]-2-(2-imino-4-oxo-1,3-thiazolidin-5-yl)acetamide;
N-(3,4-dichlorophenyl)-2-(2-imino-4-oxo-1,3-thiazolidin-5-yl)acetamide;
N-(2,4-dichlorophenyl)-2-(2-imino-4-oxo-1,3-thiazolidin-5-yl)acetamide;
N-(2,3-difluorophenyl)-2-(2-imino-4-oxo-1,3-thiazolidin-5-yl)acetamide;
N-(3,4-difluorophenyl)-2-(2-imino-4-oxo-1,3-thiazolidin-5-yl)acetamide;
N-(3-chlorophenyl)-2-(2-imino-4-oxo-1,3-thiazolidin-5-yl)acetamide;
N-(3-chloro-4-fluorophenyl)-2-(2-imino-4-oxo-1,3-thiazolidin-5-yl)acetamide;
2-(2-imino-4-oxo-1,3-thiazolidin-5-yl)-N-[4-(trifluoromethyl)benzyl]acetamide;
2-(2-imino-4-oxo-1,3-thiazolidin-5-yl)-N-(3-methylisoxazol-5-yl)acetamide;
N-(3-ethynylphenyl)-2-(2-imino-4-oxo-1,3-thiazolidin-5-yl)acetamide;
2-(2-imino-4-oxo-1,3-thiazolidin-5-yl)-N-[3-(methylthio)phenyl]acetamide;
ethyl 2-{[(2-imino-4-oxo-1,3-thiazolidin-5-yl)acetyl]amino}-4-methylthiophene-3-carboxylate;
2-(2-imino-4-oxo-1,3-thiazolidin-5-yl)-N-phenylacetamide;
N-benzyl-2-(2-imino-4-oxo-1,3-thiazolidin-5-yl)acetamide;
2-(2-imino-4-oxo-1,3-thiazolidin-5-yl)-N-[3-(trifluoromethyl)benzyl]acetamide;
2-(2-imino-4-oxo-1,3-thiazolidin-5-yl)-N-[2-(trifluoromethyl)benzyl]acetamide;
N-(4-chlorobenzyl)-2-(2-imino-4-oxo-1,3-thiazolidin-5-yl)acetamide;
N-(3-chlorobenzyl)-2-(2-imino-4-oxo-1,3-thiazolidin-5-yl)acetamide;
N-(2-chlorobenzyl)-2-(2-imino-4-oxo-1,3-thiazolidin-5-yl)acetamide;
3-{[(2-imino-4-oxo-1,3-thiazolidin-5-yl)acetyl]amino}benzamide;
ethyl 3-{[(2-imino-4-oxo-1,3-thiazolidin-5-yl)acetyl]amino}benzoate;
2-(2-imino-4-oxo-1,3-thiazolidin-5-yl)-N-(3-phenoxyphenyl)acetamide;
N-(3-benzoylphenyl)-2-(2-imino-4-oxo-1,3-thiazolidin-5-yl)acetamide;
N-(2,3-dichlorophenyl)-2-(2-imino-4-oxo-1,3-thiazolidin-5-yl)acetamide;
2-(2-imino-4-oxo-1,3-thiazolidin-5-yl)-N-(3-nitrophenyl)acetamide; N-(3-acetylphenyl)-2-(2-imino-4-oxo-1,3-thiazolidin-5-yl)acetamide;
2-(2-imino-4-oxo-1,3-thiazolidin-5-yl)-N-[3-(trifluoromethoxy)phenyl]acetamide;
2-{[(2-imino-4-oxo-1,3-thiazolidin-5-yl)acetyl]amino}-4,5,6,7-tetrahydro-1benzothiophene-3-carboxamide;
ethyl 5-ethyl-2-{[(2-imino-4-oxo-1,3-thiazolidin-5-yl)acetyl]amino}thiophene-3-carboxylate;
methyl 2-{[(2-imino-4-oxo-1,3-thiazolidin-5-yl)acetyl]amino}thiophene-3-carboxylate;
ethyl 2-{[(2-imino-4-oxo-1,3-thiazolidin-5-yl)acetyl]amino}-4,5,6,7-tetrahydro-1-benzothiophene-3-carboxylate;
ethyl 2-{[(2-imino-4-oxo-1,3-thiazolidin-5-yl)acetyl]amino}-5,6,7,8-tetrahydro-4H-cyclohepta[b]thiophene-3-carboxylate;
methyl 2-{[(2-imino-4-oxo-1,3-thiazolidin-5-yl)acetyl]amino}-6-methoxy-4,5,6,7-tetrahydro-1-benzothiophene-3-carboxylate;
methyl 2-{[(2-imino-4-oxo-1,3-thiazolidin-5-yl)acetyl]amino}-4,5,6,7-tetrahydro-1-benzothiophene-3-carboxylate;
ethyl 4,5-dimethyl-2-({[(2Z)-2-(methylimino)-4-oxo-1,3-thiazolidin-5-yl]acetyl}amino)thiophene-3-carboxylate;
ethyl 2-({[(2Z)-2-(ethylimino)-4-oxo-1,3-thiazolidin-5-yl]acetyl}amino)-4,5-dimethylthiophene-3-carboxylate;
ethyl 4,5-dimethyl-2-({[(2Z)-3-methyl-2-(methylimino)-4-oxo-1,3-thiazolidin-5-yl]acetyl}amino)thiophene-3-carboxylate;
methyl 5-tert-butyl-3-{[(2-imino-4-oxo-1,3-thiazolidin-5-yl)acetyl]amino}thiophene-2-carboxylate;
methyl 3-{[(2-imino-4-oxo-1,3-thiazolidin-5-yl)acetyl]amino}-4-methylthiophene-2-carboxylate;
ethyl 2-{[(2-imino-4-oxo-1,3-thiazolidin-5-yl)acetyl]amino}-5,6-dihydro-4H-cyclopenta[b]thiophene-3-carboxylate;
ethyl 2-{[(2-imino-4-oxo-1,3-thiazolidin-5-yl)acetyl]amino}-4-phenylthiophene-3-carboxylate;
ethyl 4-(2-furyl)-2-{[(2-imino-4-oxo-1,3-thiazolidin-5-yl)acetyl]amino}thiophene-3-carboxylate;
ethyl 4-(4-fluorophenyl)-2-{[(2-imino-4-oxo-1,3-thiazolidin-5-yl)acetyl]amino}thiophene-3-carboxylate;
ethyl 2-{[(2-imino-4-oxo-1,3-thiazolidin-5-yl)acetyl]amino}-5-methyl-4-phenylthiophene-3-carboxylate;
N-(3-cyano-4,5,6,7-tetrahydro-1-benzothien-2-yl)-2-(2-imino-4-oxo-1,3-thiazolidin-5-yl)acetamide;
methyl 2-{[(2-imino-4-oxo-1,3-thiazolidin-5-yl)acetyl]amino}benzoate;
ethyl 2-{[(2-imino-4-oxo-1,3-thiazolidin-5-yl)acetyl]amino}benzoate;
methyl 5-chloro-2-{[(2-imino-4-oxo-1,3-thiazolidin-5-yl)acetyl]amino}benzoate;
methyl 2-{[(2-imino-4-oxo-1,3-thiazolidin-5-yl)acetyl]amino}-4,5-dimethoxybenzoate;
ethyl 5-bromo-2-{[(2-imino-4-oxo-1,3-thiazolidin-5-yl)acetyl]amino}-4-methylthiophene-3-carboxylate;
tert-butyl 2-{[(2-imino-4-oxo-1,3-thiazolidin-5-yl)acetyl]amino}-5-phenylthiophene-3-carboxylate;
methyl 2-{[(2-imino-4-oxo-1,3-thiazolidin-5-yl)acetyl]amino}-5-phenylthiophene-3-carboxylate;
methyl 5-(4-chlorophenyl)-2-{[(2-imino-4-oxo-1,3-thiazolidin-5-yl)acetyl]amino}thiophene-3-carboxylate;
ethyl 2-{[(2-imino-4-oxo-1,3-thiazolidin-5-yl)acetyl]amino}-4-methyl-5-phenylthiophene-3-carboxylate;
ethyl 5-bromo-4-(bromomethyl)-2-{[(2-imino-4-oxo-1,3-thiazolidin-5-yl)acetyl]amino}thiophene-3-carboxylate;
ethyl 4-(anilinomethyl)-5-bromo-2-{[(2-imino-4-oxo-1,3-thiazolidin-5-yl)acetyl]amino}thiophene-3-carboxylate;
ethyl 5-bromo-4-{[(4-chlorophenyl)(methyl)amino]methyl}-2-{[(2-imino-4-oxo-1,3-thiazolidin-5-yl)acetyl]amino}thiophene-3-carboxylate;
ethyl 5-bromo-4-{[(4-fluorophenyl)amino]methyl}-2-{[(2-imino-4-oxo-1,3-thiazolidin-5-yl)acetyl]amino}thiophene-3-carboxylate; and
ethyl 5-bromo-4-[(cyclopentylamino)methyl]-2-{[(2-imino-4-oxo-1,3-thiazolidin-5-yl)acetyl]amino}thiophene-3-carboxylate.

Preferred compounds of Formula 1 are those that inhibit the activity of secreted frizzled related protein-1. Such compounds are of interest for the treatment of bone disorders, including osteoporosis, and for the treatment of arthritis, chronic obstructive pulmonary disease, cartilage defect repair, and leiomyoma.

In certain embodiments, the present invention therefore provides methods of treating, preventing, inhibiting, or alleviating each of the maladies listed above in a mammal, preferably in a human, comprising administering a therapeutically effective amount of a compound of Formula 1 to a patient suspected to suffer from such a malady.

In other embodiments, the invention relates to compositions comprising at least one compound of Formula 1, or a steroisomer or pharmaceutically acceptable salt thereof, and one or more pharmaceutically acceptable carriers, excipients, or diluents. Such compositions include pharmaceutical compositions for treating or controlling disease states or conditions of the bone. In certain embodiments, the compositions comprise mixtures of one or more compounds of Formula 1.

Certain of the compounds of Formula 1 contain stereogenic carbon atoms or other chiral elements and thus give rise to stereoisomers, including enantiomers and diastereomers. The invention generally relates to all stereoisomers of the compounds of Formula 1, as well as to mixtures of the stereoisomers. Throughout this application, the name of a compound without indication as to the absolute configuration of an asymmetric center is intended to embrace the individual stereoisomers as well as mixtures of stereoisomers. Reference to optical rotation [(+), (−) and (±)] is utilized to distinguish the enantiomers from one another and from the racemate. Furthermore, throughout this application, the designations R* and S* are used to indicate relative stereochemistry, employing the Chemical Abstracts convention which automatically assigns R* to the lowest numbered asymmetric center.

An enantiomer can, in some embodiments of the invention, be provided substantially free of the corresponding enantiomer. Thus, reference to an enantiomer as being substantially free of the corresponding enantiomer indicates that it is isolated or separated via separation techniques or prepared so as to be substantially free of the corresponding enantiomer. "Substantially free," as used herein, means that a significantly lesser proportion of the corresponding enantiomer is present. In preferred embodiments, less than about 90% by weight of the corresponding enantiomer is present relative to desired enantiomer, more preferably less than about 1% by weight. Preferred enantiomers can be isolated from racemic mixtures by any method known to those skilled in the art, including high performance liquid chromatography (HPLC), and the formation and crystallization of chiral salts, or preferred enantiomers, can be prepared by methods described herein. Methods for the preparation of enantiomers are described, for example, in Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); and Wilen, S. H. *Tables of Resolving Agents and Optical Resolutions* p. 268 (E. L. Eliel, Ed., Univ. of Notre Dame Press, Notre Dame, Ind. 1972), each of which is hereby incorporated by reference in its entirety.

The following synthetic schemes are designed to illustrate, but not limit, general procedures for the preparation of compounds of Formula 1. The reagents used can be either commercially obtained or can be prepared by standard procedures described in the literature.

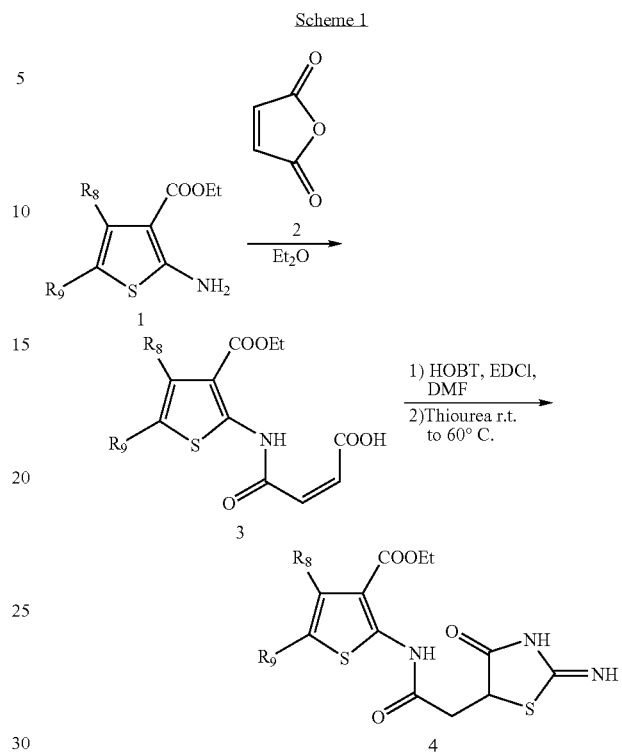

As shown in Scheme 1, appropriately substituted amino thiophene 1 can be reacted with maleic anhdride 2 in a neutral solvent, such as ether, at ambient temperature to yield the acid 3. The acid is activated with suitable activating agents, such as 1-(3-dimethylaminopropyl)-3-ethylcarbodiimide (EDCI) and 1-hydroxybenzotriazole (HOBT), and is reacted with thiourea in a solvent such as DMF, to yield iminothiazolidinone derivatives 4.

5-Bromo derivatives such as ethyl 5-bromo-2-{[(2-imino-4-oxo-1,3-thiazolidin-5-yl)acetyl]amino})-4-methylthiophene-3-carboxylate (Example 54) can be prepared by bromination of 1 using brominating agents, such as N-bromosuccinimide (NBS), in a chlorinated solvent, such as chloroform, at low temperature to yield the bromo intermediate 5, which is converted to the final product as described in Scheme 2.

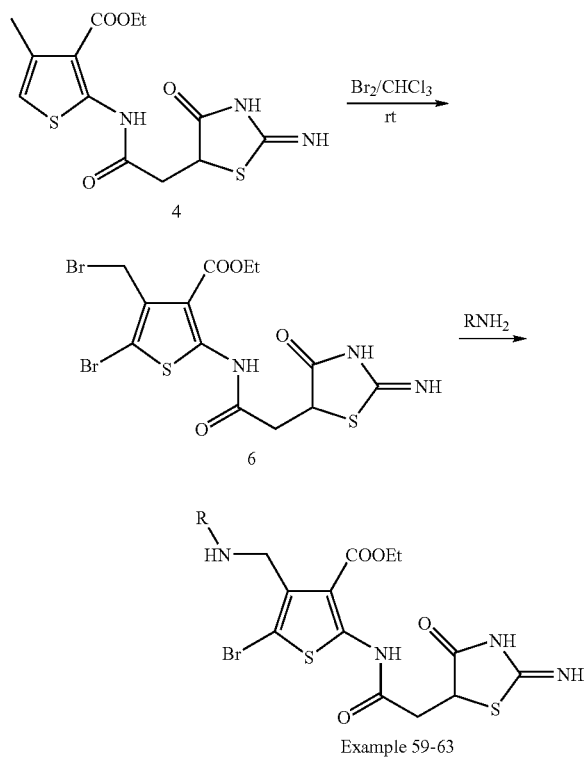

As shown in Scheme 3, substituted 4-aminomethyl derivatives, such as those of Examples 59 to 63, can be prepared by brominating a compound such as 4 with bromine in a chlorinated solvent, such as chloroform, at ambient temperature to yield the 5-bromo, 4-bromomethyl derivative 6. Reaction of 6 with various amines in a solvent such as DMF provides compounds such as those of Examples 59 to 63.

In certain embodiments, the invention relates to compositions comprising at least one compound of Formula 1, or a stereoisomer or pharmaceutically acceptable salt thereof, and one or more pharmaceutically acceptable carriers, excipients, or diluents. Such compositions are prepared in accordance with general pharmaceutical formulation procedures, such as, for example, those described in *Remingtons Pharmaceutical Sciences,* 17th edition, ed. Alfonoso R. Gennaro, Mack Publishing Company, Easton, Pa. (1985), which is incorporated herein by reference in its entirety. Pharmaceutically acceptable carriers are those carriers that are compatible with the other ingredients in the formulation and are biologically acceptable.

The compounds of Formula 1 can be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of Formula 1 can be administered rectally or vaginally in the form of a conventional suppository. For administration by intranasal or intrabronchial inhalation or insufflation, the compounds of Formula 1 can be formulated into an aqueous or partially aqueous solution, which can then be utilized in the form of an aerosol. The compounds of Formula 1 can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of Formula 1 are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age, and response pattern of the patient. The compounds can be administered orally, rectally, parenterally, or topically to the skin and mucosa. The usual daily dose depends on the specific compound, method of treatment and condition treated. The usual daily dose is 0.01-1000 mg/kg for oral application, preferably 0.5-500 mg/kg, and 0.1-100 mg/kg for parenteral application, preferably 0.5-50 mg/kg.

In certain embodiments, the present invention is directed to prodrugs of compounds of Formula 1. The term "prodrug," as used herein, means a compound that is convertible in vivo by metabolic means (e.g. by hydrolysis) to a compound of Formula 1. Various forms of prodrugs are known in the art such as those discussed in, for example, Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). *"Design and Application of Prodrugs, Textbook of Drug Design and Development*, Chapter 5, 113-191 (1991), Bundgaard, et al., *Journal of Drug Delivery Reviews*, 8:1-38(1992), Bundgaard, *J. of Pharmaceutical Sciences*, 77:285 et seq. (1988); and Higuchi and Stella (eds.) *Prodrugs as Novel Drug Delivery Systems*, American Chemical Society (1975), each of which is hereby incorporated by reference in its entirety.

The following examples are illustrative of certain embodiments of the invention and should not be considered to limit the scope of the invention.

EXAMPLE 1

Ethyl 2-{[(2-amino-4-oxo-4,5-dihydro-1,3-thiazol-5-yl) acetyl]amino}-4,5-dimethylthiophene-3-carboxylate Step 1: A solution of 2-Amino-4,5-dimethyl-thiophene-3-carboxylic acid ethyl ester (5.53 g, 27.8 mmol) in 25 mL of anhydrous ether was added dropwise to a solution of maleic anhydride (2.72 g, 27.8 mmol) in 25 mL of anhydrous ether. The reaction mixture was stirred at room temperature for 10 h. A yellow precipitate was formed. 2-(3-Carboxy-acryloylamino)-4,5-dimethyl-thiophene-3-carboxylic acid ethyl ester (5.96 g, 72% yield) was obtained as a yellow solid by filtration.

HPLC: Rt=2.8 min; MS 298 (M+H)

Step 2: To 2-(3-Carboxy-acryloylamino)-4,5-dimethyl-thiophene-3-carboxylic acid ethyl ester (2.97 g, 10.0 mmol) in 50 mL of N,N-dimethyl-formamide was added N-hydroxy-benzotriazole (1.48 g, 11.0 mmol) and 1-[3-(dimethylamino) propyl]-3-ethyl-carbodiimide hydrochloride (2.88 g, 15.0 mmol). The reaction mixture was stirred at room temperature for 10 minutes and thiourea (0.84 g, 11.0 mmol) was added. The reaction mixture was stirred at room temperature for another 30 minutes and was heated at 60° C. for 12 hours. The reaction mixture was diluted with 250 mL of ethyl acetate and was washed with 100 mL of water and 100 mL of brine. The organic layer was collected, dried over sodium sulfate and concentrated. The residue was load on a 120 g silica gel column and purified by flash chromatography (eluted with a gradient of 0 to 10% ethyl acetate/hexanes). Ethyl 2-{[(2-amino-4-oxo-4,5-dihydro-1,3-thiazol-5-yl) acetyl]amino}-4,5-dimethylthiophene-3-carboxylate (1.80 g, 51% yield) was produced.

LC/MS conditions: Aquasil C18; Mobile Phase A: 100% (0.1% Formic Acid) in water (by volume), B: 100% (0.1% Formic Acid) in CAN; Flow Rate: 0.800 mL/min.

Column Temperature: 40° C.; Injection Volume: 5 µL, UV: monitor 215, 230, 254, 280, and 300 nm; Purity is reported at 254 nm unless otherwise noted.

| Gradient Table: | |
| --- | --- |
| Time (min) | % B |
| 0 | 0 |
| 2.5 | 100 |
| 4.0 | 100 |
| 4.1 | 0 |
| 5.5 | 0 |

| MS Conditions | |
| --- | --- |
| Instrument: | Agilent MSD |
| Ionization Mode: | API-ES |
| Gas Temperature: | 350 C. |
| Drying Gas: | 13.0 L/min. |
| Nebulizer Pressure: | 55 psig |
| Polarity: | 50% positive, 50% negative |
| VCap: | 3000 V (positive), 2500 V (negative) |
| Fragmentor: | 120 (positive), 120 (negative) |
| Mass Range: | 100-1000 m/z |
| Threshold: | 150 |
| Step size: | 0.15 |
| Gain: | 1 |
| Peak width: | 0.15 min |

HPLC: Rt=2.00 min; MS 356.1 (M+H); [1]NMR (DMSO-d6): δ 10.92 (1H, s); 9.01 (1H, s); 8.79 (1H, s); 4.42 (1H, dd); 4.29 (2H, q); 3.37 (1H, dd); 2.98 (1H, dd); 2.22 (3H, s); 2.19 (3H, s); 1.32 (3H, t); MS (ESI) m/z 356; Anal. Calculated for C14H17N3O4S2: C, 47.31; H, 4.82; N, 11.82. Found: C, 47.24; H, 4.55; N, 11.75.

EXAMPLES 2 TO 53

The compounds of Examples 2 to 53 were prepared generally according to the procedures described in Example 1.

| Example No. | Compound Name |
|---|---|
| 2 | N-(3-bromophenyl)-2-(2-imino-4-oxo-1,3-thiazolidin-5-yl)acetamide |
| 3 | N-(3-fluorophenyl)-2-(2-imino-4-oxo-1,3-thiazolidin-5-yl)acetamide |
| 4 | N-(3-cyanophenyl)-2-(2-imino-4-oxo-1,3-thiazolidin-5-yl)acetamide |
| 5 | N-[3-(acetylamino)phenyl]-2-(2-imino-4-oxo-1,3-thiazolidin-5-yl)acetamide |
| 6 | N-(3,4-dichlorophenyl)-2-(2-imino-4-oxo-1,3-thiazolidin-5-yl)acetamide |
| 7 | N-(2,4-dichlorophenyl)-2-(2-imino-4-oxo-1,3-thiazolidin-5-yl)acetamide |
| 8 | N-(2,3-difluorophenyl)-2-(2-imino-4-oxo-1,3-thiazolidin-5-yl)acetamide |
| 9 | N-(3,4-difluorophenyl)-2-(2-imino-4-oxo-1,3-thiazolidin-5-yl)acetamide |
| 10 | N-(3-chlorophenyl)-2-(2-imino-4-oxo-1,3-thiazolidin-5-yl)acetamide |
| 11 | N-(3-chloro-4-fluorophenyl)-2-(2-imino-4-oxo-1,3-thiazolidin-5-yl)acetamide |
| 12 | 2-(2-imino-4-oxo-1,3-thiazolidin-5-yl)-N-[4-(trifluoromethyl)benzyl]acetamide |
| 13 | 2-(2-imino-4-oxo-1,3-thiazolidin-5-yl)-N-(3-methylisoxazol-5-yl)acetamide |
| 14 | N-(3-ethynylphenyl)-2-(2-imino-4-oxo-1,3-thiazolidin-5-yl)acetamide |
| 15 | 2-(2-imino-4-oxo-1,3-thiazolidin-5-yl)-N-[3-(methylthio)phenyl]acetamide |
| 16 | ethyl 2-{[(2-imino-4-oxo-1,3-thiazolidin-5-yl)acetyl]amino}-4-methylthiophene-3-carboxylate |
| 17 | 2-(2-imino-4-oxo-1,3-thiazolidin-5-yl)-N-phenylacetamide |
| 18 | N-benzyl-2-(2-imino-4-oxo-1,3-thiazolidin-5-yl)acetamide |
| 19 | 2-(2-imino-4-oxo-1,3-thiazolidin-5-yl)-N-[3-(trifluoromethyl)benzyl]acetamide |
| 20 | 2-(2-imino-4-oxo-1,3-thiazolidin-5-yl)-N-[2-(trifluoromethyl)benzyl]acetamide |
| 21 | N-(4-chlorobenzyl)-2-(2-imino-4-oxo-1,3-thiazolidin-5-yl)acetamide |
| 22 | N-(3-chlorobenzyl)-2-(2-imino-4-oxo-1,3-thiazolidin-5-yl)acetamide |
| 23 | N-(2-chlorobenzyl)-2-(2-imino-4-oxo-1,3-thiazolidin-5-yl)acetamide |
| 24 | 3-{[(2-imino-4-oxo-1,3-thiazolidin-5-yl)acetyl]amino}benzamide |
| 25 | ethyl 3-{[(2-imino-4-oxo-1,3-thiazolidin-5-yl)acetyl]amino}benzoate |
| 26 | 2-(2-imino-4-oxo-1,3-thiazolidin-5-yl)-N-(3-phenoxyphenyl)acetamide |
| 27 | N-(3-benzoylphenyl)-2-(2-imino-4-oxo-1,3-thiazolidin-5-yl)acetamide |
| 28 | N-(2,3-dichlorophenyl)-2-(2-imino-4-oxo-1,3-thiazolidin-5-yl)acetamide |
| 29 | 2-(2-imino-4-oxo-1,3-thiazolidin-5-yl)-N-(3-nitrophenyl)acetamide |
| 30 | N-(3-acetylphenyl)-2-(2-imino-4-oxo-1,3-thiazolidin-5-yl)acetamide |
| 31 | 2-(2-imino-4-oxo-1,3-thiazolidin-5-yl)-N-[3-(trifluoromethoxy)phenyl]acetamide |
| 32 | 2-{[(2-imino-4-oxo-1,3-thiazolidin-5-yl)acetyl]amino}-4,5,6,7-tetrahydro-1-benzothiophene-3-carboxamide |
| 33 | ethyl 5-ethyl-2-{[(2-imino-4-oxo-1,3-thiazolidin-5-yl)acetyl]amino}thiophene-3-carboxylate |
| 34 | methyl 2-{[(2-imino-4-oxo-1,3-thiazolidin-5-yl)acetyl]amino}thiophene-3-carboxylate |
| 35 | ethyl 2-{[(2-imino-4-oxo-1,3-thiazolidin-5-yl)acetyl]amino}-4,5,6,7-tetrahydro-1-benzothiophene-3-carboxylate |
| 36 | ethyl 2-{[(2-imino-4-oxo-1,3-thiazolidin-5-yl)acetyl]amino}-5,6,7,8-tetrahydro-4H-cyclohepta[b]thiophene-3-carboxylate |
| 37 | methyl 2-{[(2-imino-4-oxo-1,3-thiazolidin-5-yl)acetyl]amino}-6-methoxy-4,5,6,7-tetrahydro-1-benzothiophene-3-carboxylate |
| 38 | methyl 2-{[(2-imino-4-oxo-1,3-thiazolidin-5-yl)acetyl]amino}-4,5,6,7-tetrahydro-1-benzothiophene-3-carboxylate |
| 39 | ethyl 4,5-dimethyl-2-({[(2Z)-2-(methylimino)-4-oxo-1,3-thiazolidin-5-yl]acetyl}amino)thiophene-3-carboxylate |
| 40 | ethyl 2-({[(2Z)-2-(ethylimino)-4-oxo-1,3-thiazolidin-5-yl]acetyl}amino)-4,5-dimethylthiophene-3-carboxylate |
| 41 | ethyl 4,5-dimethyl-2-({[(2Z)-3-methyl-2-(methylimino)-4-oxo-1,3-thiazolidin-5-yl]acetyl}amino)thiophene-3-carboxylate |
| 42 | methyl 5-tert-butyl-3-{[(2-imino-4-oxo-1,3-thiazolidin-5-yl)acetyl]amino}thiophene-2-carboxylate |
| 43 | methyl 3-{[(2-imino-4-oxo-1,3-thiazolidin-5-yl)acetyl]amino}-4-methylthiophene-2-carboxylate |
| 44 | ethyl 2-{[(2-imino-4-oxo-1,3-thiazolidin-5-yl)acetyl]amino}-5,6-dihydro-4H-cyclopenta[b]thiophene-3-carboxylate |
| 45 | ethyl 2-{[(2-imino-4-oxo-1,3-thiazolidin-5-yl)acetyl]amino}-4-phenylthiophene-3-carboxylate |
| 46 | ethyl 4-(2-furyl)-2-{[(2-imino-4-oxo-1,3-thiazolidin-5-yl)acetyl]amino}thiophene-3-carboxylate |
| 47 | ethyl 4-(4-fluorophenyl)-2-{[(2-imino-4-oxo-1,3-thiazolidin-5-yl)acetyl]amino}thiophene-3-carboxylate |
| 48 | ethyl 2-{[(2-imino-4-oxo-1,3-thiazolidin-5-yl)acetyl]amino}-5-methyl-4-phenylthiophene-3-carboxylate |
| 49 | N-(3-cyano-4,5,6,7-tetrahydro-1-benzothien-2-yl)-2-(2-imino-4-oxo-1,3-thiazolidin-5-yl)acetamide |
| 50 | methyl 2-{[(2-imino-4-oxo-1,3-thiazolidin-5-yl)acetyl]amino}benzoate |
| 51 | ethyl 2-{[(2-imino-4-oxo-1,3-thiazolidin-5-yl)acetyl]amino}benzoate |
| 52 | methyl 5-chloro-2-{[(2-imino-4-oxo-1,3-thiazolidin-5-yl)acetyl]amino}benzoate |
| 53 | methyl 2-{[(2-imino-4-oxo-1,3-thiazolidin-5-yl)acetyl]amino}-4,5-dimethoxybenzoate |

EXAMPLE 54

Ethyl 5-bromo-2-{[(2-imino-4-oxo-1,3-thiazolidin-5-yl)acetyl]amino}-4-methylthiophene-3-carboxylate Step 1: To 2-Amino-4-methyl-thiophene-3-carboxylic acid ethyl ester (3.70 g, 20.0 mmol) in 50 mL of chloroform was added N-bromosuccinmide (3.60 g, 20.0 mmol) stepwise at 0° C. The reaction mixture was stirred at 0° C. for 1 hour and then diluted with 50 mL of chloroform. The reaction mixture was then washed with 100 mL of saturated sodium bicarbonate and 100 mL of brine. The organic layer was collected, dried over sodium sulfate and concentrated. The residue was load on a 120 g silica gel column and purified by flash chromatography (eluted with a gradient of 0 to 100% ethyl acetate/hexane over 8 column volumes). 2-Amino-5-bromo-4-methyl-thiophene-3-carboxylic acid ethyl ester (3.59 g, 68% yield) was obtained as a gray solid.

HPLC: Rt=2.54 min; MS 364, 366 [M+H]$^1$H NMR (DMSO-d6): δ 6.08 (2H, br); 4.30 (2H, q); 2.25 (3H, s); 1.35 (3H, t).

Step 2: Following the same procedure described in Example 1 (step 1 and step 2), Ethyl 5-bromo-2-{[(2-imino-4-oxo-1,3-thiazolidin-5-yl) acetyl]amino}-4-methylthiophene-3-carboxylate was made.

HPLC: Rt=2.25 min; MS 420 [M+H].

EXAMPLES 55-58

The compounds of Examples 55 to 58 were prepared generally according to the procedures described in Example 1.

| Example No. | Compound Name |
| --- | --- |
| 55 | tert-butyl 2-{[(2-imino-4-oxo-1,3-thiazolidin-5-yl)acetyl]amino}-5-phenylthiophene-3-carboxylate |
| 56 | methyl 2-{[(2-imino-4-oxo-1,3-thiazolidin-5-yl)acetyl]amino}-5-phenylthiophene-3-carboxylate |
| 57 | methyl 5-(4-chlorophenyl)-2-{[(2-imino-4-oxo-1,3-thiazolidin-5-yl)acetyl]amino}thiophene-3-carboxylate |
| 58 | ethyl 2-{[(2-imino-4-oxo-1,3-thiazolidin-5-yl)acetyl]amino}-4-methyl-5-phenylthiophene-3-carboxylate |

EXAMPLE 59

Ethyl 5-bromo-4-(bromomethyl)-2-{[(2-imino-4-oxo-1,3-thiazolidin-5-yl)acetyl]amino}thiophene-3-carboxylate The title compound was prepared generally according to the procedures described in Example 60.

EXAMPLE 60

Ethyl 4-(anilinomethyl)-5-bromo-2-{[(2-imino-4-oxo-1,3-thiazolidin-5-yl) acetyl]amino}thiophene-3-carboxylate Step 1: To Ethyl 2-{[(2-imino-4-oxo-1,3-thiazolidin-5-yl) acetyl]amino}-4-methylthiophene-3-carboxylate (1.80 g 5.27 mmol) in 50 mL of chloroform was added bromine (0.90 mL, 17.5 mmol). The reaction mixture was stirred at room temperature for 6 h. The reaction mixture was then diluted with methylene chloride (200 mL) and the organic solution was washed with saturated sodium bicarbonate (100 mL) and brine (100 mL). The organic layer was collected and dried over sodium sulfate and concentrated to yield ethyl 5-bromo-4-(bromomethyl)-2-{[(2-imino-4-oxo-1,3-thiazolidin-5-yl) acetyl]amino}thiophene-3-carboxylate (1.80 g, 68% yield)

Step 2: To ethyl 5-bromo-4-(bromomethyl)-2-{[(2-imino-4-oxo-1,3-thiazolidin-5-yl) acetyl]amino}thiophene-3-carboxylate (25 mg, 0.05 mmol) in N,N dimethyl formaide (1 mL) was added aniline (10 mg, 0.11 mmol). The reaction mixture was stirred at room temperature for 16 h. Then the reaction mixture was concentrated and purified by reverse phase column to yield ethyl 4-(anilinomethyl)-5-bromo-2-{[(2-imino-4-oxo-1,3-thiazolidin-5-yl)acetyl]amino}thiophene-3-carboxylate (5.0 mg, 20% yield).

HPLC: Rt=2.7 min; MS 511,513 [M+H].

EXAMPLES 61 TO 63

The compounds of Examples 61 to 63 were prepared generally according to the procedures described in Example 60.

| Example No. | Compound Name |
| --- | --- |
| 61 | ethyl 5-bromo-4-{[(4-chlorophenyl)(methyl)amino]methyl}-2-{[(2-imino-4-oxo-1,3-thiazolidin-5-yl)acetyl]amino}thiophene-3-carboxylate |
| 62 | ethyl 5-bromo-4-{[(4-fluorophenyl)amino]methyl}-2-{[(2-imino-4-oxo-1,3-thiazolidin-5-yl)acetyl]amino}thiophene-3-carboxylate |
| 63 | ethyl 5-bromo-4-[(cyclopentylamino)methyl]-2-{[(2-imino-4-oxo-1,3-thiazolidin-5-yl)acetyl]amino}thiophene-3-carboxylate |

The following table provides the HPLC retention time and mass spec data for the compounds of Examples 1 to 63.

| Example | Rt (min.) | MS |
| --- | --- | --- |
| 1 | 2.00 | 356.1 [M + H] |
| 2 | 1.84 | 327.9 [M + H] |
| 3 | 1.86 | 268 [M + H] |
| 4 | 1.59 | 275 [M + H] |
| 5 | 1.39 | 307 [M + H] |
| 6 | 1.98 | 317.9 [M + H] |
| 7 | 1.87 | 317.9 [M + H] |
| 8 | 1.63 | 286 [M + H] |
| 9 | 1.74 | 286 [M + H] |
| 10 | 1.80 | 284 [M + H] |
| 11 | 1.84 | 302 [M + H] |
| 12 | 1.84 | 332 [M + H] |
| 13 | 1.47 | 255 [M + H] |
| 14 | 1.75 | 274 [M + H] |
| 15 | 1.78 | 296 [M + H] |
| 16 | 2.05 | 342 [M + H] |
| 17 | 1.54 | 250 [M + H] |
| 18 | 1.49 | 264 [M + H] |
| 19 | 1.80 | 332 [M + H] |
| 20 | 1.83 | 332 [M + H] |
| 21 | 1.73 | 298 [M + H] |
| 22 | 1.71 | 298 [M + H] |
| 23 | 1.68 | 298 [M + H] |
| 24 | 1.27 | 293 [M + H] |
| 25 | 1.81 | 322 [M + H] |
| 26 | 2.06 | 342 [M + H] |
| 27 | 1.94 | 354 [M + H] |
| 28 | 1.84 | 317.9 [M + H] |
| 29 | 1.70 | 295 [M + H] |
| 30 | 1.55 | 292 [M + H] |
| 31 | 1.97 | 334 [M + H] |
| 32 | 2.37 | 353 [M + H] |

-continued

| Example | Rt (min.) | MS |
|---|---|---|
| 33 | 2.76 | 356 [M + H] |
| 34 | 2.34 | 314 [M + H] |
| 35 | 2.93 | 382 [M + H] |
| 36 | 2.99 | 396 [M + H] |
| 37 | 2.56 | 398 [M + H] |
| 38 | 2.79 | 368 [M + H] |
| 39 | 2.28 | 370.1 [M + H] |
| 40 | 2.36 | 384.1 [M + H] |
| 41 | 2.41 | 384.1 [M + H] |
| 42 | 2.19 | 370 [M + H] |
| 43 | 1.48 | 328 [M + H] |
| 44 | 2.20 | 368 [M + H] |
| 45 | 2.21 | 404 [M + H] |
| 46 | 2.08 | 394 [M + H] |
| 47 | 2.23 | 422 [M + H] |
| 48 | 2.32 | 418 [M + H] |
| 49 | 1.97 | 335 [M + H] |
| 50 | 1.71 | 308 [M + H] |
| 51 | 1.87 | 322 [M + H] |
| 52 | 1.95 | 342 [M + H] |
| 53 | 1.72 | 368 [M + H] |
| 54 | 2.25 | 420 [M + H] |
| 55 | 2.9 | 432 [M + H] |
| 56 | 2.4 | 390 [M + H] |
| 57 | 2.7 | 424 [M + H] |
| 58 | 2.8 | |
| 59 | 2.6 | 498,500 [M − H] |
| 60 | 2.7 | 511,513 [M + H] |
| 61 | 3.1 | 557,559 [M − H] |
| 62 | 2.7 | 529,531 [M + H] |
| 63 | 1.7 | 503,505 [M + H] |

EXAMPLE 64

Cell-Based Assay for In Vitro Measurement of SFRP-1/SARP2 Antagonist Activity

The following cell-based assay can be used to identify inhibitors of SFRP-1.

Materials and Methods

Cells

The osteosarcoma cell line, U2OS (ATCC, HTB 96), was passaged twice a week with growth medium (McCoy's SA medium containing 10% (v/v) fetal calf serum, 2 mM GlutaMAX-1, and 1% (v/v) Penicillin-Streptomycin). The cells were maintained in vented flasks at 37° C. inside a 5% $CO_2$/95% humidified air incubator. One day prior to transfection, the cells were plated with growth medium at 25,000 cells/well into 96-well plates and incubated at 37° C. overnight.

Routine Co-Transfection

The growth medium was removed, and the cells were washed once with OPTIMEM I (Gibco-BRL) medium (100 µl/well) to remove the serum and antibiotics. The wash medium was removed, and the cells were re-fed with OPTI-MEM I medium (100 µl/well). For each well of cells to be transfected, the following DNA's were diluted together in 25 µl OPTI-MEM I medium: 0.1 µg 16× TCF-tk-Luciferase reporter, 0.02 µg Wnt 3, Wnt3A, Wnt 1 or empty vector (Upstate Biotechnology), 0.075 µg hSFRP-1 or empty vector (pcDNA3.1, Invitrogen), and 0.025 µg CMV-®gal (Clonetech). For each well of cells to be transfected, 1 µl of Lipofectamine 2000 reagent (Invitrogen) was diluted in 25 µl OPTI-MEM I medium and incubated at room temperature for 5 minutes. The diluted DNA's were then combined with the diluted Lipofectamine 2000 (LF2000), and the mixture was incubated at room temperature for 20 minutes. Fifty µl of the DNA-LF 2000 mixture was added to each well, and the plate(s) were incubated at 37° C. in a 5% $CO_2$/95% humidified air incubator for 4 hours. The cells were washed once with 150 µl/well of experimental medium (phenol red-free RPMI Medium 1640 containing 2% fetal bovine serum, 2 mM GlutaMAX-1, and 1% Penicillin-Streptomycin). Finally, the cells were treated overnight at 37° C. with 200 µl/well of experimental medium containing either vehicle (typically DMSO) or diluted compound in replicates of 8 wells/compound.

Dosing

Initial single dose screening of test compounds was done at 10 µM.

Dose-response experiments were initially performed with the compounds in log increases from 1-10,000 nM. From these dose-response curves, $EC_{50}$ values were generated.

Assay

After treatment, the cells were washed twice with 150 µl/well of PBS without calcium or magnesium and were lysed with 50 µl/well of 1× cell culture lysis reagent (Promega Corporation) on a shaker at room temperature for 30 minutes. Thirty µl aliquots of the cell lysates were transferred to 96-well luminometer plates, and luciferase activity was measured in a MicroLumat PLUS luminometer (EG&G Berthold), or a Victor (PerkinElmer Life Sciences) using 100 µg/well of luciferase substrate (Promega Corporation). Following the injection of substrate, luciferase activity was measured for 10 seconds after a 1.6 second delay. Similarly, 10 µl aliquots of the cell lysates were transferred to separate 96-well luminometer plates, and 50 µl of Galacton chemiluminescent substrate (Tropix) was added to each well. The plates were covered and incubated on a rotary shaker at room temperature for one hour. ®gal activity was measured in a MicroLumat PLUS luminometer or Victor using 100 µl/well of Light Emission Accelerator (Tropix). Following the injection of the accelerator, ®gal activity was measured for 10 seconds after a 1.6 second delay. The luciferase and ®gal activity data were transferred from the luminometer to a PC and analyzed using the SAS/Excel program. After the luciferase activity was normalized to ®gal, the SAS/Excel program was used to determine the mean and standard deviation of each treatment, to analyze the data for statistical significance, and to determine EC50 values.

Large-Scale Co-Transfection

As an alternative to co-transfection in a 96 well plate, the U2OS cells were transfected in T225 flasks and the transfected cells were frozen. The frozen cells were thawed and plated on a 96 well plate and the assay was carried out as detailed above. The growth medium was removed from the T225 flasks, and the cells were washed once with OPTI-MEM I medium (approx. 25 ml/flask) to remove the serum and antibiotics. The wash medium was removed, and the cells were re-fed with OPTI-MEM I medium (59 ml/flask). For each T225 flask of cells to be transfected, the following DNA's were diluted together in 5.9 ml OPTI-MEM I medium: 70.3 µg 16×TCF-tk-Luciferase reporter, 14.06 µg WNT3, 3A or Wnt1 or empty vector, 52.8 µg hSFRP-1 or empty vector, and 17.58 µg CMV-®gal. Separately, for each flask of cells to be transfected, 354 µl of Lipofectamine 2000 reagent (Invitrogen) was diluted in 5.9 ml OPTI-MEM I medium and incubated at room temperature for 5 minutes. The diluted DNA's were then combined with the diluted Lipofectamine 2000 (LF2000), and the mixture was incubated at room temperature for 20 minutes. 11.8 ml of the DNA-LF 2000 mixture was added to each flask, and the flask(s) were incubated at 37° C. in a 5% $CO_2$/95% humidified air incubator for 4 hours. The medium was removed, and the cells were washed once with approximately 25 ml/flask of phenol red-free RPMI Medium 1640, then re-fed with 50 ml/flask of experimental medium (phenol red-free RPMI Medium 1640 containing 2% fetal bovine serum, 2 mM GlutaMAX-1, and 1% Penicillin-Streptomycin) and incubated at 37° C. overnight.

Freezing Cells

The transfected cells were washed twice with 25 ml/flask/wash of PBS without calcium or magnesium. Three ml of Trypsin-EDTA (0.05% Trypsin, 0.53 mM EDTA-4Na) was added to each flask, and the flasks were incubated at room temperature for approximately 5 minutes until the cells were rounded and detached from the surface of the flask(s). The cells were resuspended in 10 ml/flask of phenol red-free RPMI 1640 containing 10% fetal bovine serum and were pipetted up and down several times until a single cell suspension was formed. The resuspended cells were pooled and a 10 µl aliquot was removed and diluted at 1:10 in PBS. The diluted cells were counted using a hemacytometer to determine the total number of cells in the pool. The cells were transferred to sterile centrifuge tubes and pelletted at 1500 rpm in a Sorvall RC-3B refrigerated centrifuge at 4° C. for 5 minutes. The supernatant was aspirated and the cells were resuspended in cold, phenol red-free RPMI 1640 medium containing 50% FBS to a cell density of 2.5E+7 cells/ml. An equal volume of cold, 2× freezing medium (phenol red-free RPMI 1640 medium containing 50% FBS and 15% DMSO) was added slowly, dropwise to the resuspended cells with gentle mixing, resulting in a final cell density of 1.25E+7 cells/ml. The resuspended cells were placed on ice and aliquoted into sterile cryogenic vials. The vials were transferred to a Nalgene Cryo 1° C. freezing container (Nalgene catalog # 5100-0001) containing 250 ml isopropyl alcohol. The sealed container was placed in a −80° C. freezer overnight to freeze the cells at a cooling rate of −1° C./minute. The frozen cells were then transferred to a −150° C. freezer for long-term storage.

Benchtop Assay for Single Dose Confirmation of HTS Hits

A vial of frozen transfected cells was thawed, and the cells were resuspended in phenol red-free RPMI 1640 medium to a final cell density of 150,000 cells/ml. The resuspended cells were then plated in white, 96-well polystyrene tissue culture treated CulturPlates™ (Packard cat. # 6005180) at a volume of 100 µl of cell suspension/well (i.e. 15,000 cells/well). The plates were incubated at 37° C. inside a 5% $CO_2$/95% humidified air incubator for 6 hours or until the cells were attached and started to spread. Test compounds were then added to the wells (1 well/compound) and the plates were incubated at 37° C. overnight. After the overnight incubation, luciferase activity was measured using the Luc-Screen Luciferase Assay System (Tropix). Fifty µl of Luc-Screen buffer 1, warmed to room temperature, was added directly to the cells in the 96-well plates. Fifty µl of Luc-Screen buffer 2, warmed to room temperature, was then added, and the plates were incubated in the dark, at room temperature, for 10 minutes. The plates were transferred to a Packard Top Count Microplate Scintillation and Luminescence Counter (Packard), and the light emission was measured for 10 seconds after a 2 minute delay.

The luciferase activity data was transferred to a PC and analyzed using the SAS/Excel program as described above.

Analysis of Results

The luciferase data was analyzed using the SAS/Excel program. For the initial single dose experiment, if the compound treatment resulted in increased reporter activity and was specific to SFRP-1 inhibition, then the results were reported as fold induction over SFRP-1 control (see the Table below).

Compounds

A known inhibitor of GSK-3β, a key enzyme involved in the Wnt signaling pathway, served as an internal control for measurement of the cellular response to Wnt signaling. The inhibition of GSK-3 results in stabilization of β-catenin, leading to up-regulation of LEF/TCF regulated reporter genes.

| Example | Fold induction with SFRP-1 | Ratio |
|---|---|---|
| 1 | 2.5 | 2.5 |
| 2 | 2 | 1.8 |
| 3 | 1.5 | 1.3 |
| 4 | 1.3 | 1.2 |
| 5 | 1.3 | 1.2 |
| 6 | 1.7 | 1.7 |
| 7 | 1.0 | 1.0 |
| 8 | 1.1 | 1.0 |
| 9 | 1.6 | 1.5 |
| 10 | 2.2 | 2.2 |
| 11 | 1.9 | 1.7 |
| 12 | 1.1 | 1.0 |
| 13 | 1.0 | 1.0 |
| 14 | 1.8 | 1.6 |
| 15 | 1.5 | 1.2 |
| 16 | 2.0 | 1.9 |
| 17 | 1.3 | 1.0 |
| 18 | 1.2 | 1.1 |
| 19 | 1.1 | 0.9 |
| 20 | 1.2 | 1.1 |
| 21 | 1.2 | 1.0 |
| 22 | 1.2 | 1.0 |
| 23 | 1.2 | 1.0 |
| 24 | 1.2 | 1.0 |
| 25 | 1.7 | 1.4 |
| 26 | 1.5 | 1.4 |
| 27 | 1.8 | 1.5 |
| 28 | 1.2 | 1.0 |
| 29 | 1.7 | 1.4 |
| 30 | 1.2 | 1.1 |
| 31 | 1.7 | 1.5 |
| 32 | 1.0 | 1.1 |
| 33 | 1.5 | 1.7 |
| 34 | 1.2 | 1.3 |
| 35 | 1.4 | 1.6 |
| 36 | 1.5 | 1.9 |
| 37 | 1.5 | 1.7 |
| 38 | 1.3 | 1.4 |
| 39 | | |
| 40 | | |
| 41 | | |
| 42 | 1.5 | 1.7 |
| 43 | 1.0 | 1.0 |
| 44 | 1.6 | 1.5 |
| 45 | 1.1 | 1.0 |
| 46 | 1.1 | 1.0 |
| 47 | 1.1 | 1.0 |
| 48 | 1.6 | 1.8 |
| 49 | 1.6 | 1.2 |
| 50 | 1.1 | 1.0 |
| 51 | 1.1 | 1.1 |
| 52 | 1.1 | 1.1 |
| 53 | 1.0 | 1.0 |
| 54 | 2.6 | 2.6 |
| 55 | 1.2 | 0.9 |
| 56 | 0.9 | 0.9 |
| 57 | 0.9 | 0.8 |
| 58 | 0.7 | 0.7 |
| 59 | 1.1 | 1.4 |
| 60 | 2.7 | 2.4 |
| 61 | 0.7 | 1.0 |
| 62 | 2.0 | 2.2 |
| 63 | 1.5 | 1.1 |

We claim:
1. A compound of Formula 1:

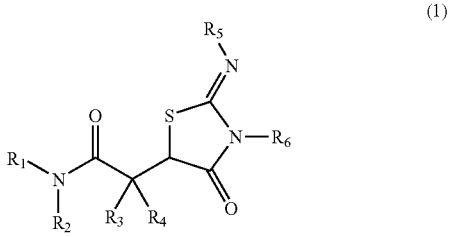

or a pharmaceutically acceptable salt thereof,
wherein
$R_2$ is hydrogen; straight chain alkyl of 1 to 8 carbon atoms; branched chain alkyl of 3 to 12 carbons atoms; alkenyl of 2 to 8 carbon atoms; cycloalkyl or bicycloalkyl of 3 to 12 carbon atoms; heterocycloalkyl or heterobicycloalkyl of 3 to 12 ring atoms having 1 to 3 heteroatoms independently selected from nitrogen, oxygen, and sulfur; aryl of 6 to 10 carbon atoms; or heteroaryl of 5 to 10 ring atoms having 1 to 3 heteroatoms independently selected from nitrogen, oxygen, and sulfur;

$R_3$, $R_4$, $R_5$, and $R_6$ are, independently, hydrogen; straight chain alkyl of 1 to 8 carbon atoms; branched chain alkyl of 3 to 12 carbons atoms; straight chain alkenyl of 2 to 8 carbon atoms; branched chain alkenyl of 3 to 12 carbons atoms; straight chain alkynyl of 2 to 8 carbon atoms; branched chain alkynyl of 5 to 12 carbons atoms; or cycloalkyl of 3 to 12 carbon atoms;

$R_1$ is a group of the following Formula (2):

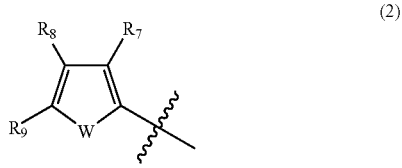

wherein
$R_7$ is hydrogen; straight chain alkyl of 1 to 8 carbon atoms; branched chain alkyl of 3 to 12 carbons atoms; alkenyl of 2 to 8 carbon atoms; cycloalkyl of 3 to 12 carbon atoms; heterocycloalkyl of 3 to 12 ring atoms having 1 to 3 heteroatoms independently selected from nitrogen, oxygen, and sulfur; aryl of 6 to 10 carbon atoms; heteroaryl of 5 to 10 ring atoms having 1 to 3 heteroatoms independently selected from nitrogen, oxygen, and sulfur; —C(O)OR; —CONR$_2$; —N(R)COR; or halogen;

R is straight chain alkyl of 1 to 8 carbon atoms; or branched chain alkyl of 3 to 12 carbons atoms;

$R_8$ and $R_9$ are, independently, hydrogen; straight chain alkyl of 1 to 8 carbon atoms; branched chain alkyl of 3 to 12 carbons atoms; alkenyl of 2 to 8 carbon atoms; cycloalkyl of 3 to 12 carbon atoms; heterocycloalkyl of 3 to 12 ring atoms having 1 to 3 heteroatoms independently selected from oxygen, nitrogen, and sulfur; aryl of 6 to 10 carbon atoms; heteroaryl of 5 to 10 ring atoms having 1 to 3 heteroatoms independently selected from nitrogen, oxygen, and sulfur; —C(O)OR; —CONR$_2$; —N(R)COR; or halogen;

or $R_8$ and $R_9$, together with the carbon atoms to which they are attached, form a cycloalkyl, heterocycloalkyl, aryl, or heteroaryl group of 5 to 9 atoms, wherein the heterocycloalkyl and heteroaryl groups have 1 to 3 heteroatoms independently selected from oxygen, nitrogen, and sulfur; and W is S.

2. The compound of claim 1 wherein the straight chain alkyl, cycloalkyl, bicycloalkyl, heterocycloalkyl, heterobicycloalkyl, aryl and heteroaryl groups of $R_2$ is optionally substituted with 1 to 5 substituents independently selected from straight chain alkyl of 1 to 8 carbon atoms; branched chain alkyl of 3 to 12 carbon atoms; alkenyl of 2 to 8 carbon atoms; alkynyl of 2 to 8 carbon atoms; cycloalkyl of 3 to 12 carbon atoms; heterocycloalkyl of 3 to 12 ring atoms having 1 to 3 heteroatoms independently selected from nitrogen, oxygen, and sulfur; aryl of 6 to 10 carbon atoms; heteroaryl of 5 to 10 ring atoms having 1 to 3 heteroatoms independently selected from nitrogen, oxygen, and sulfur; alkoxy of 1 to 8 carbon atoms, perfluoroalkoxy of 1 to 8 carbon atoms; phenyloxy; alkylthio of 1 to 8 carbon atoms; acyl of 2 to 7 carbon atoms; phenylcarbonyl; —C(O)OR; —CONR$_2$; —N(R)COR; halogen; cyano; and nitro; and each R is independently selected from hydrogen, straight chain alkyl of 1 to 8 carbon atoms; and branched chain alkyl of 3 to 12 carbons atoms.

3. The compound of claim 2 wherein the straight chain alkyl, cycloalkyl, bicycloalkyl, heterocycloalkyl, and heterobicycloalkyl substituents on the straight chain alkyl, cycloalkyl, bicycloalkyl, heterocycloalkyl, heterobicycloalkyl, aryl, and heteroaryl groups of $R_2$ is optionally substituted with 1 to 5 substituents independently selected from aryl of 6 to 10 carbon atoms; arylamino of 6 to 10 carbon atoms; haloarylamino of 6 to 10 carbon atoms; alkylamino of 1 to 8 carbon atoms; cycloalkylamino of 3 to 12 carbon atoms; arlyoxy of 6 to 10 carbon atoms; alkoxy of 1 to 8 carbon atoms; arylthio of 6 to 10 carbon atoms; alkylthio of 1 to 8 carbon atoms; Br; Cl; and Fl.

4. The compound of claim 2 wherein the aryl and heteroaryl substituents on the straight chain alkyl, cycloalkyl, bicycloalkyl, heterocycloalkyl, heterobicycloalkyl, aryl, and heteroaryl groups of $R_2$ is optionally substituted with 1 to 5 substituents independently selected from alkyl of 1 to 8 carbon atoms; perfuloroalkyl of 1 to 8 carbon atoms; Fl; Cl; and Br.

5. The compound of claim 1 wherein the straight chain alkyl groups of $R_3$, $R_4$, $R_5$, and $R_6$ are optionally substituted with 1 to 5 substituents independently selected from aryl of 6 to 10 carbon atoms; heteroaryl of 5 to 10 ring atoms having 1 to 3 heteroatoms independently selected from oxygen, nitrogen, and sulfur; cycloalkyl of 3 to 12 carbon atoms; and heterocycloalkyl of 3 to 12 ring atoms having 1 to 3 heteroatoms independently selected from oxygen, nitrogen, and sulfur.

6. The compound of claim 5 wherein the aryl, heteroaryl, cycloalkyl, and heterocycloalkyl substituents on the straight chain alkyl groups of $R_3$, $R_4$, $R_5$, and $R_6$ are themselves optionally substituted with one to five substituents independently selected from halogen; straight chain alkyl of 1 to 6 carbon atoms; branched chain alkyl of 3 to 6 carbon atoms; perfluoroalkyl of 1 to 3 carbon atoms; perfluoroalkoxy of 1 to 3 carbon atoms; alkoxy of 1 to 6 carbon atoms; aminoalkyl of 1 to 8 carbon atoms; N,N-dialklyamino of 1 to 8 carbon atoms; —C(O)OR; —CONR$_2$; and —N(R)COR; and R is straight chain alkyl of 1 to 8 carbon atoms; or branched chain alkyl of 3 to 12 carbons atoms.

7. The compound of claim 1 wherein $R_2$ is hydrogen.

8. The compound of claim 7 wherein $R_3$ and $R_4$ are each hydrogen.

9. The compound of claim 8 wherein $R_5$ and $R_6$ are, independently, hydrogen or straight chain alkyl of 1 to 3 carbon atoms.

10. The compound of claim 1 wherein the straight chain alkyl, cycloalkyl, heterocycloalkyl, aryl, and heteroaryl groups of $R_7$ are optionally substituted with 1 to 5 substituents independently selected from straight chain alkyl of 1 to 8 carbon atoms; aryl of 6 to 10 carbon atoms; halogen; alkoxy of 1 to 6 carbon atoms; perfluoroalkyl of 1 to 3 carbon atoms; perfluoroalkoxy of 1 to 3 carbon atoms; aminoalkyl of 1 to 8 carbon atoms; N,N-dialkylamino of 1 to 8 carbon atoms; —C(O)OR; —CONR$_2$; and —N(R)COR.

11. The compound of claim 10 wherein the straight chain alkyl substituents on the straight chain alkyl, cycloalkyl, heterocycloalkyl, aryl, and heteroaryl groups of $R_7$ are themselves optionally substituted with 1 to 5 substituents independently selected from alkoxy of 1 to 6 carbon atoms; aminoalkyl of 1 to 8 carbon atoms; N,N-dialkylamino of 1 to 8 carbon atoms; —C(O)OR; —CONR$_2$; and —N(R)COR.

12. The compound of claim 1 wherein the straight chain alkyl groups of $R_8$ and $R_9$ are optionally substituted with 1 to 5 substituents independently selected from aryl of 6 to 10 carbon atoms; arylamino of 6 to 10 carbon atoms; alkylamino of 1 to 8 carbon atoms; arlyoxy of 6 to 10 carbon atoms; alkoxy of 1 to 8 carbon atoms; arylthio of 6 to 10 carbon atoms; and alkylthio of 1 to 8 carbon atoms.

13. The compound of claim 12 wherein the straight chain alkyl substituents on the straight chain alkyl groups of $R_8$ and $R_9$ are themselves optionally substituted with 1 to 5 substituents independently selected from alkoxy of 1 to 6 carbon atoms; aminoalkyl of 1 to 8 carbon atoms; N,N-dialkylamino of 1 to 8 carbon atoms; —C(O)OR; —CONR$_2$; and —N(R)COR.

14. The compound of claim 1 wherein the cycloalkyl, heterocycloalkyl, aryl and heteroaryl groups of $R_8$ and $R_9$ are optionally substituted with 1 to 5 substituents independently selected from straight chain alkyl of 1 to 8 carbon atoms; halogen; alkoxy of 1 to 6 carbon atoms; perfluoroalkyl of 1 to 3 carbon atoms; perfluoroalkoxy of 1 to 3 carbon atoms; aminoalkyl of 1 to 8 carbon atoms; N,N-dialkylamino of 1 to 8 carbon atoms; —C(O)OR; —CONR$_2$; and —N(R)COR.

15. The compound of claim 14 wherein the straight chain alkyl substituents on the cycloalkyl, heterocycloalkyl, aryl, and heteroaryl groups of $R_8$ and $R_9$ are themselves optionally substituted with 1 to 5 substituents independently selected from alkoxy of 1 to 6 carbon atoms; aminoalkyl of 1 to 8 carbon atoms; N,N-dialkylamino of 1 to 8 carbon atoms; —C(O)OR; —CONR$_2$; and —N(R)COR.

16. The compound of claim 1 wherein the cycloalkyl, heterocycloalkyl, aryl, and heteroaryl groups formed from $R_8$ and $R_9$ together with the carbon atoms to which they are attached are optionally substituted with 1 to 5 substituents independently selected from straight chain alkyl of 1 to 8 carbon atoms; halogen; alkoxy of 1 to 6 carbon atoms; perfluoroalkyl of 1 to 3 carbon atoms; perfluoroalkoxy of 1 to 3 carbon atoms; aminoalkyl of 1 to 8 carbon atoms; N,N-dialkylamino of 1 to 8 carbon atoms; —C(O)OR; —CONR$_2$; and —N(R)COR.

17. The compound of claim 16 wherein the straight chain alkyl substituents on the cycloalkyl, heterocycloalkyl, aryl, and heteroaryl groups formed from $R_8$ and $R_9$ together with the carbon atoms to which they are attached, are themselves optionally substituted with 1 to 5 substituents independently selected from alkoxy of 1 to 6 carbon atoms; aminoalkyl of 1 to 8 carbon atoms; N,N-dialkylamino of 1 to 8 carbon atoms; —C(O)OR; —CONR$_2$; and —N(R)COR.

18. The compound of claim 1 wherein $R_2$ is hydrogen.

19. The compound of claim 1 wherein $R_3$ and $R_4$ are each hydrogen.

20. The compound of claim 1 wherein $R_5$ and $R_6$ are, independently, hydrogen or straight chain alkyl of 1 to 3 carbon atoms.

21. The compound of claim 1 which is ethyl 2-{[(2-amino-4-oxo-4,5-dihydro-1,3-thiazol-5-yl)acetyl]amino}-4,5-dimethylthiophene-3-carboxylate;

2-{[(2-imino-4-oxo-1,3-thiazolidin-5-yl)acetyl]amino}-4,5,6,7-tetrahydro-1-benzothiophene-3-carboxamide;

ethyl 5-ethyl-2-{[(2-imino-4-oxo-1,3-thiazolidin-5-yl)acetyl]amino}thiophene-3-carboxylate;

methyl 2-{[(2-imino-4-oxo-1,3-thiazolidin-5-yl)acetyl]amino}thiophene-3-carboxylate;

ethyl 2-{[(2-imino-4-oxo-1,3-thiazolidin-5-yl)acetyl]amino}-4,5,6,7-tetrahydro-1-benzothiophene-3-carboxylate;

ethyl 2-{[(2-imino-4-oxo-1,3-thiazolidin-5-yl)acetyl]amino}-5,6,7,8-tetrahydro-4H-cyclohepta[b]thiophene-3-carboxylate;

methyl 2-{[(2-imino-4-oxo-1,3-thiazolidin-5-yl)acetyl]amino}-6-methoxy-4,5,6,7-tetrahydro-1-benzothiophene-3-carboxylate;

methyl 2-{[(2-imino-4-oxo-1,3-thiazolidin-5-yl)acetyl]amino}-4,5,6,7-tetrahydro-1-benzothiophene-3-carboxylate;

ethyl 4,5-dimethyl-2-({[(2Z)-2-(methylimino)-4-oxo-1,3-thiazolidin-5-yl]acetyl}amino)thiophene-3-carboxylate;

ethyl 2-({[(2Z)-2-(ethylimino)-4-oxo-1,3-thiazolidin-5-yl]acetyl}amino)-4,5-dimethylthiophene-3-carboxylate;

ethyl 4,5-dimethyl-2-({[(2Z)-3-methyl-2-(methylimino)-4-oxo-1,3-thiazolidin-5-yl]acetyl}amino)thiophene-3-carboxylate;

methyl 5-tert-butyl-3-{[(2-imino-4-oxo-1,3-thiazolidin-5-yl)acetyl]amino}thiophene-2-carboxylate;

methyl 3-{[(2-imino-4-oxo-1,3-thiazolidin-5-yl)acetyl]amino}-4-methylthiophene-2-carboxylate;

ethyl 2-{[(2-imino-4-oxo-1,3-thiazolidin-5-yl)acetyl]amino}-5,6-dihydro-4H-cyclopenta[b]thiophene-3-carboxylate;

ethyl 2-{[(2-imino-4-oxo-1,3-thiazolidin-5-yl)acetyl]amino}-4-phenylthiophene-3-carboxylate;

ethyl 4-(2-furyl)-2-{[(2-imino-4-oxo-1,3-thiazolidin-5-yl)acetyl]amino}thiophene-3-carboxylate;

ethyl 4-(4-fluorophenyl)-2-{[(2-imino-4-oxo-1,3-thiazolidin-5-yl)acetyl]amino}thiophene-3-carboxylate;

ethyl 2-{[(2-imino-4-oxo-1,3-thiazolidin-5-yl)acetyl]amino}-5-methyl-4-phenylthiophene-3-carboxylate;

ethyl 5-bromo-2-{[(2-imino-4-oxo-1,3-thiazolidin-5-yl)acetyl]amino}-4-methylthiophene-3-carboxylate;

tert-butyl 2-{[(2-imino-4-oxo-1,3-thiazolidin-5-yl)acetyl]amino}-5-phenylthiophene-3-carboxylate;

methyl 2-{[(2-imino-4-oxo-1,3-thiazolidin-5-yl)acetyl]amino}-5-phenylthiophene-3-carboxylate;

methyl 5-(4-chlorophenyl)-2-{[(2-imino-4-oxo-1,3-thiazolidin-5-yl)acetyl]amino}thiophene-3-carboxylate;

ethyl 2-{[(2-imino-4-oxo-1,3-thiazolidin-5-yl)acetyl]amino}-4-methyl-5-phenylthiophene-3-carboxylate;

ethyl 5-bromo-4-(bromomethyl)-2-{[(2-imino-4-oxo-1,3-thiazolidin-5-yl)acetyl]amino}thiophene-3-carboxylate;

ethyl 4-(anilinomethyl)-5-bromo-2-{[(2-imino-4-oxo-1,3-thiazolidin-5-yl)acetyl]amino}thiophene-3-carboxylate;

ethyl 5-bromo-4-{[(4-chlorophenyl)(methyl)amino]methyl}-2-{[(2-imino-4-oxo-1,3-thiazolidin-5-yl)acetyl]amino}thiophene-3-carboxylate;

ethyl 5-bromo-4-{[(4-fluorophenyl)amino]methyl}-2-{[(2-imino-4-oxo-1,3-thiazolidin-5-yl)acetyl]amino}thiophene-3-carboxylate; or ethyl 5-bromo-4-[(cyclopentylamino)methyl]-2-{[(2-imino-4-oxo-1,3-thiazolidin-5-yl)acetyl]amino}thiophene-3-carboxylate;

or a pharmaceutically acceptable salt thereof.

22. A composition comprising at least one compound of claim 1 or a pharmaceutically acceptable salt thereof and one or more pharmaceutically acceptable excipients, diluents, or carriers.

23. A method for treating a patient suffering from osteoporosis, arthritis, chronic obstructive pulmonary disease, cartilage defect repair, or leiomyoma comprising administering to the patient a therapeutically effective amount of at least one compound of claim 1.

24. The method of claim 23 wherein the patient suffers from osteoporosis.

* * * * *